US009533151B2

(12) United States Patent
Craig

(10) Patent No.: US 9,533,151 B2
(45) Date of Patent: *Jan. 3, 2017

(54) MICROBURST ELECTRICAL STIMULATION OF CRANIAL NERVES FOR THE TREATMENT OF MEDICAL CONDITIONS

(71) Applicant: Catholic Healthcare West, Phoenix, AZ (US)

(72) Inventor: Arthur D. Craig, Phoenix, AZ (US)

(73) Assignee: DIGNITY HEALTH, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,428

(22) Filed: Jan. 10, 2014

(65) Prior Publication Data

US 2014/0128938 A1    May 8, 2014

Related U.S. Application Data

(63) Continuation of application No. 12/400,970, filed on Mar. 10, 2009, now Pat. No. 8,660,666, which is a
(Continued)

(51) Int. Cl.
*A61N 1/36*      (2006.01)
*A61N 1/05*      (2006.01)
(Continued)

(52) U.S. Cl.
CPC ......... *A61N 1/36139* (2013.01); *A61N 1/0551* (2013.01); *A61N 1/3605* (2013.01);
(Continued)

(58) Field of Classification Search
None
See application file for complete search history.

(56) References Cited

U.S. PATENT DOCUMENTS 3,760,812 A    9/1973 Timm et al.
3,796,221 A    3/1974 Hagfors
(Continued)

FOREIGN PATENT DOCUMENTS

AU    2007/233135 A1    10/2007
AU    2007/233205 A1    10/2007
(Continued)

OTHER PUBLICATIONS

Bachman, et al., "Effects of Vagal Volleys and Serotonin on Units of Cingulate Cortex in Monkeys," Brian Research, vol. 130 (1997) (pp. 253-269).
(Continued)

*Primary Examiner* — Erica Lee
(74) *Attorney, Agent, or Firm* — CF3; Stephen Eisenmann

(57) ABSTRACT

Disclosed herein are methods, systems, and apparatus for treating a medical condition in a patient using an implantable medical device by applying an electrical signal characterized by having a number of pulses per microburst, an interpulse interval, a microburst duration, and an interburst period to a portion of a cranial nerve of said patient, wherein at least one of the number of pulses per microburst, the interpulse interval, the microburst duration, or the interburst period is selected to enhance cranial nerve evoked potentials.

16 Claims, 11 Drawing Sheets

Related U.S. Application Data continuation of application No. 11/693,451, filed on Mar. 29, 2007, now Pat. No. 8,615,309.

(60) Provisional application No. 60/787,680, filed on Mar. 29, 2006.

(51) Int. Cl.
  *A61B 5/0476* (2006.01)
  *A61B 5/00* (2006.01)

(52) U.S. Cl.
  CPC ..... *A61N 1/36053* (2013.01); *A61N 1/36064* (2013.01); *A61N 1/36082* (2013.01); *A61N 1/36114* (2013.01); *A61N 1/36178* (2013.01); *A61B 5/0476* (2013.01); *A61B 5/4094* (2013.01)

(56) References Cited

U.S. PATENT DOCUMENTS

| | | |
|---|---|---|
| 4,073,048 A | 2/1978 | Ditcher |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,509,946 A | 4/1985 | McFarlane |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 4,979,511 A | 12/1990 | Terry, Jr. |
| 5,025,807 A | 6/1991 | Zabara |
| 5,073,048 A | 12/1991 | Adachi et al. |
| 5,081,987 A | 1/1992 | Nigam |
| 5,150,508 A | 9/1992 | St. Denis |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,073,048 A | 6/2000 | Kieval et al. |
| 6,083,249 A | 7/2000 | Familoni |
| 6,101,412 A | 8/2000 | Duhaylongsod |
| 6,104,955 A | 8/2000 | Bourgeois |
| 6,104,959 A | 8/2000 | Spertell |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja et al. |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |

(56) References Cited

U.S. PATENT DOCUMENTS

| | | |
|---|---|---|
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,631,293 B2 | 10/2003 | Lyden |
| 6,656,125 B2 | 12/2003 | Misczynski et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,737,875 B2 | 5/2004 | Davis et al. |
| 6,754,530 B2 | 6/2004 | Bakels et al. |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,788,975 B1 | 9/2004 | Whitehurst et al. |
| 6,793,670 B2 | 9/2004 | Osorio et al. |
| 6,819,956 B2 | 11/2004 | DiLorenzo |
| 6,825,767 B2 | 11/2004 | Humbard |
| 6,826,428 B1 | 11/2004 | Chen et al. |
| 6,832,114 B1 | 12/2004 | Whitehurst et al. |
| 6,843,870 B1 | 1/2005 | Bluger |
| 6,853,862 B1 | 2/2005 | Marchal et al. |
| 6,885,888 B2 | 4/2005 | Rezai |
| 6,895,278 B1 | 5/2005 | Gordon |
| 6,900,421 B2 | 5/2005 | Varma |
| 6,901,292 B2 | 5/2005 | Hrdlicka et al. |
| 6,901,293 B2 | 5/2005 | Rogers et al. |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,940,255 B2 | 9/2005 | Loch |
| 6,944,501 B1 | 9/2005 | Pless |
| 6,949,929 B2 | 9/2005 | Gray et al. |
| 6,958,705 B2 | 10/2005 | Lebel et al. |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,052,983 B2 | 5/2006 | Park et al. |
| 7,054,686 B2 | 5/2006 | MacDonald |
| 7,076,307 B2 | 7/2006 | Boveja et al. |
| 7,085,605 B2 | 8/2006 | Bluger et al. |
| 7,091,231 B2 | 8/2006 | Donde et al. |
| 7,107,097 B2 | 9/2006 | Stern et al. |
| 7,142,923 B2 | 11/2006 | North et al. |
| 7,146,217 B2 | 12/2006 | Firlik et al. |
| 7,149,574 B2 | 12/2006 | Yun et al. |
| 7,164,941 B2 | 1/2007 | Misczynski et al. |
| 7,167,750 B2 | 1/2007 | Knudson et al. |
| 7,177,678 B1 | 2/2007 | Osorio et al. |
| 7,184,837 B2 | 2/2007 | Goetz |
| 7,188,053 B2 | 3/2007 | Nikitin et al. |
| 7,191,012 B2 | 3/2007 | Boveja et al. |
| 7,204,833 B1 | 4/2007 | Osorio et al. |
| 7,209,787 B2 | 4/2007 | DiLorenzo |
| 7,209,790 B2 | 4/2007 | Thompson et al. |
| 7,231,254 B2 | 6/2007 | DiLorenzo |
| 7,236,822 B2 | 6/2007 | Dobak, III |
| 7,236,830 B2 | 6/2007 | Gliner |
| 7,236,831 B2 | 6/2007 | Firlik et al. |
| 7,239,912 B2 | 7/2007 | Dobak, III |
| 7,239,926 B2 | 7/2007 | Goetz |
| 7,242,983 B2 | 7/2007 | Frei et al. |
| 7,242,984 B2 | 7/2007 | DiLorenzo |
| 7,249,281 B2 | 7/2007 | Shirley et al. |
| 7,252,090 B2 | 8/2007 | Goetz |
| 7,254,439 B2 | 8/2007 | Misczynski et al. |
| 7,263,405 B2 | 8/2007 | Boveja et al. |
| 7,277,758 B2 | 10/2007 | DiLorenzo |
| 7,277,761 B2 | 10/2007 | Shelchuk |
| 7,289,545 B2 | 10/2007 | Charles |
| 7,289,844 B2 | 10/2007 | Misczynski et al. |
| 7,292,890 B2 | 11/2007 | Whitehurst et al. |
| 7,299,091 B2 | 11/2007 | Barrett et al. |
| 7,321,793 B2 | 1/2008 | Ben Ezra et al. |
| 7,340,302 B1 | 3/2008 | Falkenberg et al. |
| 7,340,306 B2 | 3/2008 | Barrett et al. |
| 7,346,395 B2 | 3/2008 | Lozano et al. |
| 7,352,285 B2 | 4/2008 | Sakama et al. |
| 7,363,076 B2 | 4/2008 | Yun et al. |
| 7,369,897 B2 | 5/2008 | Boveja et al. |
| 7,377,930 B2 | 5/2008 | Loughran |
| 7,395,117 B2 | 7/2008 | Mazar et al. |
| 7,418,292 B2 | 8/2008 | Shafer |
| 7,422,555 B2 | 9/2008 | Hess |
| 7,422,555 B2 | 9/2008 | Zabara |
| 7,437,196 B2 | 10/2008 | Wyler et al. |
| 7,444,183 B2 | 10/2008 | Knudson et al. |
| 7,444,184 B2 | 10/2008 | Boveja et al. |
| 7,454,245 B2 | 11/2008 | Armstrong et al. |
| 7,454,251 B2 | 11/2008 | Rezai et al. |
| 7,454,359 B2 | 11/2008 | Rosenfeld et al. |
| 7,483,743 B2 | 1/2009 | Mann et al. |
| 7,483,747 B2 | 1/2009 | Gliner et al. |
| 7,485,095 B2 | 2/2009 | Shusterman |
| 7,493,168 B2 | 2/2009 | Rezai |
| 7,496,409 B2 | 2/2009 | Greenhut et al. |
| 7,509,170 B2 | 3/2009 | Zhang et al. |
| 7,512,438 B2 | 3/2009 | Fischell et al. |
| 7,519,430 B2 | 4/2009 | Von Arx et al. |
| 7,532,938 B2 | 5/2009 | Machado et al. |
| 7,541,191 B2 | 6/2009 | Duic |
| 7,542,800 B2 | 6/2009 | Libbus et al. |
| 7,547,284 B2 | 6/2009 | Brainard, II |
| 7,551,958 B2 | 6/2009 | Libbus et al. |
| 7,561,921 B2 | 7/2009 | Phillips et al. |
| 7,565,199 B2 | 7/2009 | Sheffield et al. |
| 7,565,200 B2 | 7/2009 | Wyler et al. |
| 7,577,481 B2 | 8/2009 | Firlik et al. |
| 7,596,413 B2 | 9/2009 | Libbus et al. |
| 7,601,115 B2 | 10/2009 | Riehl |
| 7,603,174 B2 | 10/2009 | De Ridder |
| 7,606,622 B2 | 10/2009 | Reeve |
| 7,610,083 B2 | 10/2009 | Drew et al. |
| 7,613,515 B2 | 11/2009 | Knudson et al. |
| 7,617,002 B2 | 11/2009 | Goetz |

(56) References Cited

U.S. PATENT DOCUMENTS

| | | |
|---|---|---|
| 7,620,455 B2 | 11/2009 | Maschino |
| 7,620,456 B2 | 11/2009 | Gliner et al. |
| 7,623,926 B2 | 11/2009 | Rossing et al. |
| 7,623,927 B2 | 11/2009 | Rezai |
| 7,623,928 B2 | 11/2009 | DiLorenzo |
| 7,624,293 B2 | 11/2009 | Osorio et al. |
| 7,630,757 B2 | 12/2009 | Dorfmeister et al. |
| 7,630,773 B2 | 12/2009 | Seeberger et al. |
| 7,634,317 B2 | 12/2009 | Ben-David et al. |
| 7,640,063 B2 | 12/2009 | Rezai et al. |
| 7,643,293 B2 | 1/2010 | Chu |
| 7,661,933 B2 | 2/2010 | Ohya et al. |
| 7,672,730 B2 | 3/2010 | Firlik et al. |
| 7,672,733 B2 | 3/2010 | Zhou et al. |
| 7,676,263 B2 | 3/2010 | Harris et al. |
| 7,684,866 B2 | 3/2010 | Fowler et al. |
| 7,685,005 B2 | 3/2010 | Riff et al. |
| 7,689,276 B2 | 3/2010 | Dobak |
| 7,697,991 B2 | 4/2010 | Machado et al. |
| 7,697,993 B2 | 4/2010 | Gilkerson et al. |
| 7,706,866 B2 | 4/2010 | Zhang et al. |
| 7,715,919 B2 | 5/2010 | Osorio et al. |
| 7,715,924 B2 | 5/2010 | Rezai et al. |
| 7,725,196 B2 | 5/2010 | Machado et al. |
| 7,729,773 B2 | 6/2010 | Sloan |
| 7,742,820 B2 | 6/2010 | Wyler et al. |
| 7,747,325 B2 | 6/2010 | Dilorenzo |
| 7,747,551 B2 | 6/2010 | Snyder |
| 7,756,584 B2 | 7/2010 | Sheffield et al. |
| 7,761,145 B2 | 7/2010 | Virag et al. |
| 7,764,988 B2 | 7/2010 | Drew et al. |
| 7,769,465 B2 | 8/2010 | Matos |
| 7,778,704 B2 | 8/2010 | Rezai |
| 7,778,711 B2 | 8/2010 | Ben-David et al. |
| 7,783,349 B2 | 8/2010 | Libbus et al. |
| 7,801,611 B2 | 9/2010 | Persen et al. |
| 7,805,199 B2 | 9/2010 | KenKnight et al. |
| 7,831,301 B2 | 11/2010 | Webb et al. |
| 7,831,305 B2 | 11/2010 | Gliner |
| 7,831,308 B2 | 11/2010 | Rezai et al. |
| 7,832,305 B2 | 11/2010 | Mahendra et al. |
| 7,833,174 B2 | 11/2010 | Rezai et al. |
| 7,835,796 B2 | 11/2010 | Maschino et al. |
| 7,844,334 B2 | 11/2010 | Maile et al. |
| 7,844,338 B2 | 11/2010 | Knudson et al. |
| 7,853,329 B2 | 12/2010 | DiLorenzo |
| 7,856,264 B2 | 12/2010 | Firlik et al. |
| 7,856,272 B2 | 12/2010 | Nikitin et al. |
| 7,865,237 B2 | 1/2011 | Machado et al. |
| 7,885,709 B2 | 2/2011 | Ben-David |
| 7,889,069 B2 | 2/2011 | Fifolt et al. |
| 7,890,159 B2 | 2/2011 | Zhang et al. |
| 7,890,185 B2 | 2/2011 | Cohen et al. |
| 7,899,540 B2 | 3/2011 | Maschino et al. |
| 7,904,161 B2 | 3/2011 | Osypka |
| 7,908,009 B2 | 3/2011 | Wyler et al. |
| 7,912,537 B2 | 3/2011 | Lee et al. |
| 7,917,206 B2 | 3/2011 | Frei et al. |
| 7,917,225 B2 | 3/2011 | Wyler et al. |
| 7,930,035 B2 | 4/2011 | DiLorenzo |
| 7,933,646 B2 | 4/2011 | Frei et al. |
| 7,945,316 B2 | 5/2011 | Giftakis et al. |
| 7,945,333 B2 | 5/2011 | Jacobson |
| 7,949,401 B2 | 5/2011 | Fowler et al. |
| 7,949,404 B2 | 5/2011 | Hill |
| 7,962,218 B2 | 6/2011 | Balzer et al. |
| 7,962,220 B2 | 6/2011 | Kolafa et al. |
| 7,974,693 B2 | 7/2011 | Ben-David et al. |
| 7,979,137 B2 | 7/2011 | Tracey et al. |
| 7,983,759 B2 | 7/2011 | Stahmann et al. |
| 7,986,997 B2 | 7/2011 | Elsner et al. |
| 7,991,625 B2 | 8/2011 | Rosenfeld et al. |
| 8,014,865 B2 | 9/2011 | Najafi et al. |
| 8,036,736 B2 | 10/2011 | Snyder et al. |
| 8,041,419 B2 | 10/2011 | Giftakis et al. |
| 8,046,069 B2 | 10/2011 | Kramer et al. |
| 8,046,075 B2 | 10/2011 | Rezai |
| 8,050,767 B2 | 11/2011 | Sheffield et al. |
| 8,065,011 B2 | 11/2011 | Echauz et al. |
| 8,065,012 B2 | 11/2011 | Firlik et al. |
| 8,068,918 B2 | 11/2011 | Vallapureddy et al. |
| 8,096,954 B2 | 1/2012 | Stahmann et al. |
| 8,108,033 B2 | 1/2012 | Drew et al. |
| 8,108,038 B2 | 1/2012 | Giftakis et al. |
| 8,108,046 B2 | 1/2012 | Giftakis et al. |
| 8,108,048 B2 | 1/2012 | Masoud |
| 8,111,150 B2 | 2/2012 | Miller et al. |
| 8,112,148 B2 | 2/2012 | Giftakis et al. |
| 8,112,153 B2 | 2/2012 | Giftakis et al. |
| 8,123,668 B2 | 2/2012 | Annest et al. |
| 8,126,529 B2 | 2/2012 | Johnson et al. |
| 8,126,568 B2 | 2/2012 | Gliner |
| 8,137,269 B2 | 3/2012 | Sheikhzadeh-Nadjar et al. |
| 8,150,508 B2 | 4/2012 | Craig |
| 8,155,742 B2 | 4/2012 | Ball et al. |
| 8,165,682 B2 | 4/2012 | Gopalsami et al. |
| 8,170,668 B2 | 5/2012 | Ettori et al. |
| 8,175,705 B2 | 5/2012 | Libbus |
| 8,187,181 B2 | 5/2012 | Osorio et al. |
| 8,209,009 B2 | 6/2012 | Giftakis et al. |
| 8,209,018 B2 | 6/2012 | Osorio et al. |
| 8,211,033 B2 | 7/2012 | Siejko et al. |
| 8,214,043 B2 | 7/2012 | Matos |
| 8,219,188 B2 | 7/2012 | Craig |
| 8,280,505 B2 | 10/2012 | Craig |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka et al. |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0036780 A1 | 2/2003 | Barrett et al. |
| 2003/0040774 A1 | 2/2003 | Terry et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0195574 A1 | 10/2003 | Osorio et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0024428 A1 | 2/2004 | Barrett et al. |
| 2004/0036377 A1 | 2/2004 | Mezinis |
| 2004/0039424 A1 | 2/2004 | Merritt et al. |
| 2004/0039427 A1 | 2/2004 | Barrett et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |

(56) References Cited

U.S. PATENT DOCUMENTS

| | | |
|---|---|---|
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199210 A1 | 10/2004 | Shelchuk |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0254612 A1 | 12/2004 | Ezra et al. |
| 2004/0254616 A1 | 12/2004 | Rossing et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197675 A1 | 9/2005 | David et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0251220 A1 | 11/2005 | Barrett et al. |
| 2005/0251222 A1 | 11/2005 | Barrett et al. |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja et al. |
| 2006/0015153 A1 | 1/2006 | Gliner et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0095090 A1 | 5/2006 | De Ridder |
| 2006/0100667 A1 | 5/2006 | Machado et al. |
| 2006/0100668 A1 | 5/2006 | Ben-David et al. |
| 2006/0100671 A1* | 5/2006 | Ridder .................. 607/45 |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |

(56) References Cited

U.S. PATENT DOCUMENTS

| | | |
|---|---|---|
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1* | 8/2006 | Armstrong et al. ............... 607/2 |
| 2006/0173494 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0200208 A1 | 9/2006 | Terry et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224188 A1 | 10/2006 | Libbus et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0247719 A1 | 11/2006 | Maschino et al. |
| 2006/0247722 A1 | 11/2006 | Maschino et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271108 A1* | 11/2006 | Libbus et al. ................... 607/2 |
| 2006/0271409 A1 | 11/2006 | Rosenfeld et al. |
| 2006/0293720 A1 | 12/2006 | DiLorenzo |
| 2006/0293721 A1 | 12/2006 | Tarver et al. |
| 2007/0021786 A1* | 1/2007 | Parnis et al. ...................... 607/2 |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci et al. |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156179 A1 | 7/2007 | S.E. |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0233193 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0255374 A1 | 11/2007 | Kolafa et al. |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson et al. |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |

(56) References Cited

U.S. PATENT DOCUMENTS

| | | |
|---|---|---|
| 2008/0255582 A1 | 10/2008 | Harris |
| 2009/0054795 A1 | 2/2009 | Misczynski et al. |
| 2009/0076567 A1 | 3/2009 | Fowler et al. |
| 2009/0171405 A1 | 7/2009 | Craig |
| 2009/0177252 A1 | 7/2009 | Craig |
| 2012/0191158 A1 | 7/2012 | Craig |

FOREIGN PATENT DOCUMENTS

| | | |
|---|---|---|
| AU | 2012202405 A1 | 5/2012 |
| AU | 2012202408 A1 | 5/2012 |
| BR | 2116 | 7/2011 |
| BR | 0709844-8 | 7/2011 |
| CA | 2339971 A1 | 2/2000 |
| CA | 2653110 A1 | 10/2007 |
| CA | 2653112 A1 | 10/2007 |
| EP | 0402683 A2 | 12/1990 |
| EP | 0713714 A2 | 5/1996 |
| EP | 0944411 A1 | 9/1999 |
| EP | 1070518 A2 | 1/2001 |
| EP | 1120130 A2 | 8/2001 |
| EP | 1139861 A1 | 10/2001 |
| EP | 1145736 A2 | 10/2001 |
| EP | 1202775 A1 | 5/2002 |
| EP | 1304135 A2 | 4/2003 |
| EP | 1483020 A1 | 12/2004 |
| EP | 1486232 A2 | 12/2004 |
| EP | 1595497 A1 | 11/2005 |
| EP | 1634617 A1 | 3/2006 |
| EP | 1647300 A2 | 4/2006 |
| EP | 1745818 A1 | 1/2007 |
| EP | 2004283 A1 | 12/2008 |
| EP | 2007477 A1 | 12/2008 |
| EP | 2026874 A1 | 2/2009 |
| GB | 2026870 A | 2/1980 |
| GB | 2079610 A | 1/1982 |
| IL | 194406 A | 8/2012 |
| IL | 194407 | 4/2016 |
| JP | 11-514268 | 12/1999 |
| JP | 2001-505441 A | 4/2001 |
| JP | 2003-180847 A | 7/2003 |
| JP | 2004-524125 A | 8/2004 |
| JP | 2009/503279 A | 1/2009 |
| JP | 2009/503285 A | 1/2009 |
| JP | 2011-514268 A | 5/2011 |
| WO | WO-93/01862 A1 | 2/1993 |
| WO | WO-93/02744 A1 | 2/1993 |
| WO | WO-93/21824 A1 | 11/1993 |
| WO | WO-94/00185 A1 | 1/1994 |
| WO | WO-94/00188 A1 | 1/1994 |
| WO | WO-94/17771 A2 | 8/1994 |
| WO | WO-98/25688 A1 | 6/1998 |
| WO | WO-99/56822 A1 | 11/1999 |
| WO | WO-00/40143 A1 | 7/2000 |
| WO | WO-00/64336 A1 | 11/2000 |
| WO | WO-01/05467 A1 | 1/2001 |
| WO | WO-01/08749 A1 | 2/2001 |
| WO | WO-03/076010 A1 | 9/2003 |
| WO | WO-03/085546 A1 | 10/2003 |
| WO | WO-2004/036377 A2 | 4/2004 |
| WO | WO-2004/064918 A1 | 8/2004 |
| WO | WO-2004/069330 A1 | 8/2004 |
| WO | WO-2004/071575 A1 | 8/2004 |
| WO | WO-2004/075982 A1 | 9/2004 |
| WO | WO-2004/112894 A1 | 12/2004 |
| WO | WO-2005/007120 A2 | 1/2005 |
| WO | WO-2005/007232 A2 | 1/2005 |
| WO | WO-2005/028026 A1 | 3/2005 |
| WO | WO-2005/053788 A1 | 6/2005 |
| WO | WO-2005/067599 A2 | 7/2005 |
| WO | WO-2005/101282 A2 | 10/2005 |
| WO | WO-2006/014760 A1 | 2/2006 |
| WO | WO-2006/019764 A2 | 2/2006 |
| WO | WO-2006/019822 A2 | 2/2006 |
| WO | WO-2006/050144 A1 | 5/2006 |
| WO | WO-2006/118793 A2 | 11/2006 |
| WO | WO-2006/122148 A2 | 11/2006 |
| WO | WO-2007/066343 A2 | 6/2007 |
| WO | WO-2007/072425 A2 | 6/2007 |
| WO | WO-2007/115103 A1 | 10/2007 |
| WO | WO-2007/115113 A1 | 10/2007 |
| WO | WO-2007/115118 A1 | 10/2007 |
| WO | WO-2007/124126 A2 | 11/2007 |
| WO | WO-2007/124190 A2 | 11/2007 |
| WO | WO-2007/124192 A1 | 11/2007 |
| WO | WO-2007/142523 A1 | 12/2007 |

OTHER PUBLICATIONS

Bohning, et al., "Feasibility of Vagal Nerve Stimulation—Synchronized Blood Oxygenation Level-Dependent Functional MRI," A Journal of Clinical and Laboratory Research: Investigative Radiology, vol. 36, No. 8 (Aug. 2001) (pp. 470-479).

Boon, et al., "Programmed and Magnet-Induced Vagus Nerve Stimulation for Refractory Epilepsy," Journal of Clinical Neurophysiology, vol. 18, No. 5 (2001) (pp. 402-407).

Clark, et al., "Enhanced Recognition Memory Following Vagus Nerve Stimulation in Human Subjects," Nature Neuroscience, vol. 2, No. 1 (Jan. 1999) (pp. 93-98).

Clark, et al., "Posttraining Electrical Stimulation of Vagal Afferents with Concomitant Vagal Efferent Inactivation Enhances Memory Storage Process in the Rat," Neurobiology of Learning and Memory, vol. 70 (1998) Art No. NL983863 (pp. 364-373).

Craig, A.D. "Mechanisms of thalamic pain; central neuropathic pain; focus on poststroke pain." IASP Press, Seattle, Washington (2007).

Craig, A.D. "Vagal input to lateral area 3a in cat cortex." J. Neurophysiol. 90, pp. 143-154 (Jan. 15, 2003).

Craig, A.D. (BUD), "Distribution of Trigeminothalamic and Spinothalamic Lamina I Terminations in the Macaque Monkey," The Journal of Comparative Neurology, vol. 477 (2004) (pp. 119-148).

DeGiorgo, et al., "Vagus Nerve Stimulation: Analysis of Device Parameters in 154 Patients During the Long-Term XE5 Study," Epilepsia, vol. 42, No. 8 (2001) (pp. 1017-1020).

DeVous, et al., "Effects of Vagus Nerve Stimulation on Regional Cerebral Blood Flow in Treatment-Resistant Depression," National Institute of Mental Health—42nd Annual NCDEU Meeting: Poster Session II; Poster Abstracts, Jun. 10-13, 2002, 1 page.

Dodrill, et al., "Effects of Vagal Nerve Stimulation on Cognition and Quality of Life in Epilepsy," Epilepsy and Behavior, vol. 2 (2001) (pp. 46-53).

Fanselow, et al., "Reduction of Pentylenetetrazole-Induced Seizure Activity in Awake Rats by Seizure-Triggered Trigeminal Nerve Stimulation," The Journal of Neuroscience, vol. 20, No. 21 (Nov. 2001) (p. 8160-8168).

Fromes, et al., "Clinical Utility of On-Demand Magnet use with Vagus Nerve Stimulation," AES Proceedings (pp. 117).

George, et al., "Open Trial of VNS Therapy in Severe Anxiety Disorders," 156th American Psychiatric Association Annual Meeting; May 12-23, 2003.

George, et al., "Vagus Nerve Stimulation: A New Tool for Brian Research and Therapy," Society of Biological Psychiatry, vol. 47 (2000) (pp. 287-295).

Hallowitz, et al., "Effects of Vagal Trolleys on Units of Intralaminar and Juxtalaminar Thalamic Nuclei in Monkeys," Brian Research, vol. 130 (1977) (pp. 271-286).

Harry, et al., "Balancing Act: Noise is the Key to Restoring the Body's Sense of Equalibrium," IEEE Spectrum (Apr. 2005) (pp. 37-41).

Henry, et al., "Brain Blood-Flow Alternation Induced by Therapeutic Vagus Nerve Stimulation in Partial Epilepsy: I. Actur Effects at High and Low Levels of Stimulation," Epilepsia, vol. 29, No. 9 (1998) (pp. 984-990).

Henry, T.R., "Therapeutic Mechanisms of Vagus Nerve Stimulation," Neurology, vol. 59, Suppl. 4 (Sep. 2002) (pp. S3-S14).

(56) References Cited

OTHER PUBLICATIONS

Ito, et al., "Forebrain Projections of the Vagal Responsive Site in the Thalamic Parafascicular Nucleus in Monkey," Presentation 305.2, Nov. 13, 2005, Washington D.C.
Ito, et al., Vagal-Evoked Activity in the Parafascicular Nucleus of the Primate Thalamus; J. Neurophysiol 94, May 31, 2005 (pp. 2976-2982).
King, M.D., "Effects of Short-Term Vagus Nerve Stimulation (VNS) on FOS Expression in Rat Brian Nuclei," 58th Annual Scientific Convention of the Society of Biological Psychiatry, (May 2003).
Klabunde, R.E. "Electrocardiogram (EKG, ECG)." Cardiovascular Physiology Concepts. http://www.cvphysiology.com/Arrhythmias/A009.htm. Revised Apr. 6, 2007.
Klepper, et al., "VNS Therapy Shows Potential Benefit in Patients with Migraine an Chronic Daily Headache Afte 3 to 6 Months of Treatment (Preliminary Results)," 45th Annual Scientific Meeting of the American Headache Society (Jun. 2003).
Koo, B., "EEG Changes With Vagus Nerve Stimulationn," Journal of Clinical Neurophysiology, vol. 18, No. 5 (Sep. 2001) (pp. 434-441).
Labar, D., "Vagus Nerve Stimulation for 1 Year in 269 Patients on Unchanged Antiepilectic Drugs," Seizure, vol. 13 (2004) (pp. 392-398).
Liebman, et al., "Improvement in Cognitive Function After Vagal Nerve Stimulator Implantation," Epilepsia, vol. 39, Suppl. 6 (1998) (1 page).
Lockard, et al., "Feasibility and Safety of Vagal Stimulation in Monkey Model," Epilepsia, vol. 31, Supp. 2) (1990) (pp. S20-S26).
Malow, et al., "Vagus Nerve Stimulation Reduces Daytime Sleepiness in Epilepsy Patients," Neurology 57 (2001) (pp. 879-884).
McClintock, P., "Can Noise Actually Boost Brian Power," Physics World Jul. 2002 (pp. 20-21).
Mori, et al., "Noise-Induced Entrinment and Stochastic Resonance in Human Brian Waves," Physical Review Letters vol. 88, No. 21 (2002) (pp. 218101-1-218101-4).
Rugg-Gunn, et al., "Cardiac Arrhythmias in Focal Epilepsy: a Prospective Long-Term Study," www.thelancet.com, vol. 364 (2004) (pp. 2212-2219).
Rutecki, P., "Anatomical Physiological, and Theroetical Basis for the Antiepileptic Effect of Vagus Nerve Stimulation," Epilepsia, vol. 31, Suppl. 2, (1990) (pp. S1-S6).
Sahin, et al., "Improved Nerve Cuff Electrode Recording with Subthreshold Anodic Currents," IEEE Transactions on Biomedical Engineering, vol. 45, No. 8 (ug 1998) (pp. 1044-1050).
Schachter, et al., "Progress in Epilepsy Research: Vagus Nerve Stimulation," Epilepsia, vol. 39, No. 7 (1998) (pp. 677-686).
Tatum, et al., "Vagus Nerve Stimulation and Drug Reduction," Neurology, vol. 56, No. 4 (Feb. 2001) (pp. 561-563).
Tatum, et al., "Ventricular Asystole During Vagus Nerve Stimulation for Epilepsy in Humans," Amerian Academy of Neurology (1999) (pp. 1267 See also pp. 1117, 1166, and 1265).
Terry, et al., "The Implantable Neurocyernetic Prosthesis System," Pacing and Clinical Electrophysiology, vol. 14, No. 1 (Jan. 1991) (pp. 86-93).
Tubbs, et al., "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag (2004).
Valdez-Cruz, et al., "Chronic Stimulation of the Cat Vagus Nerve Effect on Sleep and Behavior," Progress in Neuro-Psychopharmacology & Biological Psychiatry, vol. 26 (2002) (pp. 113-118).
Vonck, et al., "The Mechanism of Action of Vagus Nerve Stimulaiton for Refractory Epilepsy—The current Status," Journal of Neurophysiology, vol. 18, No. 5 (2001) (pp. 394-401).
Ward, et al., "Treatment-Refractory Obsessive-Compulsive Disorder: Potential Benefit of VNS Therapy," 23rd Annual Conference of the Anxiety Disorders Association of America (2007).
Woodbury, et al., "Vagal Stimulation Reduces the Severity of Maximal Electroshock Seizures in Intact Rats. Use of a Cuff Electrode for Stimulation and Recording," Pacing and Clinical Electrophysiology, vol. 14 (Jan. 1991) (pp. 1005-1012).
Zabara, J., "Inhibition of Experimental Seizures in Canines by Repetivie Vagal Stimulation," Epilepsia, vol. 33, No. 6 (1992) (pp. 1005-1012).
International Preliminary Report on Patentability issued Sep. 30, 2008 by the International Searching Authority for Application PCT/US2007/065537, which was filed Mar. 29, 2007 (Inventor—Arthur D. Craig; Applicant—Catholic Healthcare West) (pp. 1-7).
International Search Report issued Aug. 31, 2007 by the International Searching Authority for Application PCT/US2007/065537, which was filed Mar. 29, 2007(Inventor—Arthur D. Craig; Applicant—Catholic Healthcare West) (pp. 1-5).
Written Opinion issued Aug. 31, 2007 by the International Searching Authority for Application PCT/US2007/065537, which was filed Mar. 29, 2007 (Inventor—Arthur D. Craig; Applicant—Catholic Healthcare West) (pp. 1-6).
Amendment and Response to Final Office Action filed Oct. 10, 2011 for U.S. Appl. No. 11/693,421, filed Mar. 29, 2007 (Inventor—Arthur D. Craig; Applicant—Dignity Health) (pp. 1-18).
Amendment and Response to Non-Final Office Action filed Feb. 11, 2011 for U.S. Appl. No. 11/693,421, filed Mar. 29, 2007 (Inventor—Arthur D. Craig; Applicant—Dignity Health) (pp. 1-9).
Amendment and Response to Restriction Requirement filed Jun. 18, 2010 for U.S. Appl. No. 11/693,421, filed Mar. 29, 2007 (Inventor—Arthur D. Craig; Applicant—Dignity Health) (pp. 1-10).
Final Office Action issued Apr. 8, 2011 for U.S. Appl. No. 11/693,421, filed Mar. 29, 2007 (Inventor—Arthur D. Craig; Applicant—Dignity Health) (pp. 1-8).
Issue Notification issued Mar. 14, 2012 for U.S. Appl. No. 11/693,421, filed Mar. 29, 2007 (Inventor—Arthur D. Craig; Applicant—Dignity Health) (pp. 1-1).
Non-Final Office Action issued Aug. 12, 2010 for U.S. Appl. No. 11/693,421, filed Mar. 29, 2007 (Inventor—Arthur D. Craig; Applicant—Dignity Health) (pp. 1-9).
Notice of Allowance issued Dec. 13, 2011 for U.S. Appl. No. 11/693,421, filed Mar. 29, 2007 (Inventor—Arthur D. Craig; Applicant—Dignity Health) (pp. 1-8).
Restriction Requirement issued Mar. 18, 2010 for U.S. Appl. No. 11/693,421, filed Mar. 29, 2007 (Inventor—Arthur D. Craig; Dignity Health) (pp. 1-11).
Amendment and Response to Final Office Action filed Apr. 5, 2012 for U.S. Appl. No. 12/400,893, filed Mar. 10, 2009 (Inventor—Arthur D. Craig; Applicant—Dignity Health) (pp. 1-20).
Amendment and Response to Non-Final Office Action filed Aug. 23, 2011 for U.S. Appl. No. 12/400,893, filed Mar. 10, 2009 (Inventor—Arthur D. Craig; Applicant—Dignity Health) (pp. 1-18).
Amendment and Response to Non-Final Office Action filed Jun. 17, 2010 for U.S. Appl. No. 12/400,893, filed Mar. 10, 2009 (Inventor—Arthur D. Craig; Applicant—Dignity Health) (pp. 1-13).
Amendment in Response to Final Office Action filed Feb. 8, 2011 for U.S. Appl. No. 12/400,893, filed Mar. 10, 2009 (Inventor—Arthur D. Craig; Applicant—Dignity Health) (pp. 1-12).
Examiner Interview Summary Record issued May 12, 2010 for U.S. Appl. No. 12/400,893, filed Mar. 10, 2009 (Inventor—Arthur D. Craig; Applicant—Dignity Health) (pp. 1-3).
Final Office Action issued Aug. 10, 2010 for U.S. Appl. No. 12/400,893, filed Mar. 10, 2009 (Inventor—Arthur D. Craig; Applicant—Dignity Health) (pp. 1-10).
Final Office Action issued Nov. 18, 2011 for U.S. Appl. No. 12/400,893, filed Mar. 10, 2009 (Inventor—Arthur D. Craig; Applicant—Dignity Health) (pp. 1-9).
Issue Notification issued Sep. 12, 2012 for U.S. Appl. No. 12/400,893, filed Mar. 10, 2009 (Inventor—Arthur D. Craig; Applicant—Dignity Health) (pp. 1-1).
Non-Final Office Action issued Feb. 15, 2011 for U.S. Appl. No. 12/400,893, filed Mar. 10, 2009 (Inventor—Arthur D. Craig; Applicant—Dignity Health) (pp. 1-9).
Non-Final Office Action issued Mar. 17, 2010 for U.S. Appl. No. 12/400,893, filed Mar. 10, 2009 (Inventor—Arthur D. Craig; Applicant—Dignity Health) (pp. 1-9).

(56) References Cited

OTHER PUBLICATIONS

Notice of Allowance issued Jun. 8, 2012 for U.S. Appl. No. 12/400,893, filed Mar. 10, 2009 (Inventor—Arthur D. Craig; Applicant—Dignity Health) (pp. 1-8).
Request for Continued Examination filed Feb. 8, 2011 for U.S. Appl. No. 12/400,893, filed Mar. 10, 2009 (Inventor—Arthur D. Craig; Applicant—Dignity Health) (pp. 1-3).
Supplemental Non-Final Office Action issued Feb. 23, 2011 for U.S. Appl. No. 12/400,893, filed Mar. 10, 2009 (Inventor—Arthur D. Craig; Applicant—Dignity Health) (pp. 1-9).
Preliminary Amendment filed Apr. 3, 2012 for U.S. Appl. No. 13/438,645, filed Apr. 3, 2012 (Inventor—Arthur D. Craig; Applicant—Dignity Health) (pp. 1-9).
Restriction/Election Requirement issued Feb. 11, 2013 for U.S. Appl. No. 13/438,645, filed Apr. 3, 2012 (Inventor—Arthur D. Craig; Applicant—Dignity Health) (pp. 1-5).
Response to Restriction/Election Requirement filed Apr. 10, 2013 for U.S. Appl. No. 13/438,645, filed Apr. 3, 2012 (Inventor—Arthur D. Craig; Applicant—Dignity Health) (pp. 1-11).
Non-Final Office Action issued Jun. 19, 2013 for U.S. Appl. No. 13/438,645, filed Apr. 3, 2012 (Inventor—Arthur D. Craig; Applicant—Dignity Health) (pp. 1-18).
Response to Non-Final Office Action filed Sep. 19, 2013 for U.S. Appl. No. 13/438,645, filed Apr. 3, 2012 (Inventor—Arthur D. Craig; Applicant—Dignity Health) (pp. 1-13).
Final Office Action issued Nov. 6, 2013 for U.S. Appl. No. 13/438,645, filed Apr. 3, 2012 (Inventor—Arthur D. Craig; Applicant—Dignity Health) (pp. 1-13).
Response to Final Office Action filed Feb. 6, 2014 for U.S. Appl. No. 13/438,645, filed Apr. 3, 2012 (Inventor—Arthur D. Craig; Applicant—Dignity Health) (pp. 1-14).
Request for Continued Examination filed Feb. 6, 2014 for U.S. Appl. No. 13/438,645, filed Apr. 3, 2012 (Inventor—Arthur D. Craig; Applicant—Dignity Health) (pp. 1-3).
Non-Final Office Action issued Mar. 21, 2014 for U.S. Appl. No. 13/438,645, filed Apr. 3, 2012 (Inventor—Arthur D. Craig; Applicant—Dignity Health) (pp. 1-12).
International Preliminary Report on Patentability issued Sep. 30, 2008 for PCT/US2007/065531, which was filed Mar. 29, 2007 (Inventor—Arthur D. Craig; Applicant—Dignity Health) (pp. 1-7).
International Search Report and Written Opinion issued Sep. 14, 2007 for PCT/US2007/065531, which was filed Mar. 29, 2007 (Inventor—Arthur D. Craig; Applicant—Dignity Health) (pp. 1-10).
Advisory Action issued Jun. 15, 2011 for U.S. Appl. No. 11/693,499, filed Mar. 29, 2007 (Inventor—Arthur D. Craig; Applicant—Dignity Health) (pp. 1-3).
Amendment After Non-Final Office Action filed Aug. 16, 2010 for U.S. Appl. No. 11/693,499, filed Mar. 29, 2007 (Inventor—Arthur D. Craig; Applicant—Dignity Health) (pp. 1-8).
Amendment and Response to Non-Final Office Action filed Mar. 14, 2012 for U.S. Appl. No. 11/693,499, filed Mar. 29, 2007 (Inventor—Arthur D. Craig; Applicant—Dignity Health) (pp. 1-15).
Amendment and Response to Supplemental Final Office Action filed May 27, 2011 for U.S. Appl. No. 11/693,499, filed Mar. 29, 2007 (Inventor—Arthur D. Craig; Applicant—Dignity Health) (pp. 1-18).
Examiner Interview Summary Record issued May 11, 2010 for U.S. Appl. No. 11/693,499, filed Mar. 29, 2007 (Inventor—Arthur D. Craig; Applicant—Dignity Health) (pp. 1-3).
Final Office Action issued Sep. 28, 2010 for U.S. Appl. No. 11/693,499, filed Mar. 29, 2007 (Inventor—Arthur D. Craig; Applicant—Dignity Health) (pp. 1-15).
Issue Notification issued Jun. 20, 2012 for U.S. Appl. No. 11/693,499, filed Mar. 29, 2007 (Inventor—Arthur D. Craig; Applicant—Dignity Health) (pp. 1-1).
Non-Final Office Action issued Mar. 16, 2010 for U.S. Appl. No. 11/693,499, filed Mar. 29, 2007 (Inventor—Arthur D. Craig; Applicant—Dignity Health) (pp. 1-8).
Non-Final Office Action issued Oct. 14, 2011 for U.S. Appl. No. 11/693,499, filed Mar. 29, 2007 (Inventor—Arthur D. Craig; Applicant—Dignity Health) (pp. 1-10).
Notice of Allowance issued Apr. 3, 2012 for U.S. Appl. No. 11/693,499, filed Mar. 29, 2007 (Inventor—Arthur D. Craig; Applicant—Dignity Health) (pp. 1-4).
Response to Final Office Action filed Sep. 1, 2011 for U.S. Appl. No. 11/693,499, filed Mar. 29, 2007 (Inventor—Arthur D. Craig; Applicant—Dignity Health) (pp. 1-18).
Supplemental Final Office Action issued Mar. 1, 2011 for U.S. Appl. No. 11/693,499, filed Mar. 29, 2007 (Inventor—Arthur D. Craig; Applicant—Dignity Health) (pp. 1-14).
Non-Final Office Action issued Apr. 19, 2010 for U.S. Appl. No. 12/401,026, filed Mar. 10, 2009 (Inventor—Arthur D. Craig; Applicant—Dignity Health) (pp. 1-18).
Amendment and Response to Non-Final Office Action filed Aug. 19, 2010 for U.S. Appl. No. 12/401,026, filed Mar. 10, 2009 (Inventor—Arthur D. Craig; Applicant—Dignity Health) (pp. 1-24).
Final Office Action issued on Nov. 15, 2010 for U.S. Appl. No. 12/401,026, filed Mar. 10, 2009 (Inventor—Arthur D. Craig; Applicant—Dignity Health) (pp. 1-17).
Amendment and Response to Final Office Action filed May 9, 2011 for U.S. Appl. No. 12/401,026, filed Mar. 10, 2009 (Inventor—Arthur D. Craig; Applicant—Dignity Health) (pp. 1-22).
Request for Continued Examination filed May 9, 2011 for U.S. Appl. No. 12/401,026, filed Mar. 10, 2009 (Inventor—Arthur D. Craig; Applicant—Dignity Health) (pp. 1-3).
Non-Final Office Action issued Jun. 19, 2013 for U.S. Appl. No. 12/401,026, filed Mar. 10, 2009 (Inventor—Arthur D. Craig; Applicant—Dignity Health) (pp. 1-13).
Response to Non-Final Office Action filed Sep. 19, 2013 for U.S. Appl. No. 12/401,026, filed Mar. 10, 2009 (Inventor—Arthur D. Craig; Applicant—Dignity Health) (pp. 1-17).
Notice of Allowance issued Jan. 13, 2014 for U.S. Appl. No. 12/401,026, filed Mar. 10, 2009 (Inventor—Arthur D. Craig; Applicant—Dignity Health) (pp. 1-8).
International Preliminary Report on Patentability issued Sep. 30, 2008 by the International Searching Authority for Application PCT/US2007/065518, which was filed Mar. 29, 2007 (Inventor—Arthur D. Craig; Applicant—Catholic Healthcare West) (pp. 1-7).
International Search Report issued Aug. 30, 2007 by the International Searching Authority for Application PCT/US2007/065518, which was filed Mar. 29, 2007 (Inventor—Arthur D. Craig; Applicant—Catholic Healthcare West) (pp. 1-4).
Written Opinion issued Aug. 30, 2007 by the International Searching Authority for Application PCT/US2007/065518, which was filed Mar. 29, 2007 (Inventor—Arthur D. Craig; Applicant—Catholic Healthcare West) (pp. 1-6).
Non-Final Office Action issued Apr. 21, 2010 for U.S. Appl. No. 11/693,451, filed Mar. 29, 2007 (Inventor—Arthur D. Craig; Applicant—Dignity Health) (pp. 1-17).
Amendment and Response filed Aug. 23, 2010 for U.S. Appl. No. 11/693,451, filed Mar. 29, 2007 (Inventor—Arthur D. Craig; Applicant—Dignity Health) (pp. 1-20).
Final Office Action issued on Oct. 22, 2010 for U.S. Appl. No. 11/693,451, filed Mar. 29, 2007 (Inventor—Arthur D. Craig; Applicant—Dignity Health) (pp. 1-15).
Applicant Argument/Remarks made in an Amendment received Apr. 22, 2011 by the United States Patent and Trademark Office for U.S. Appl. No. 11/693,451, filed Mar. 29, 2007 (Inventor—Arthur D. Craig; Applicant—Dignity Health) (pp. 1-12).
Non-Final Office Action issued Jul. 27, 2012 for U.S. Appl. No. 11/693,451, filed Mar. 29, 2007 (Inventor—Arthur D. Craig; Applicant—Dignity Health) (pp. 1-23).
Amendment and Response to Non-Final Office Action filed on Jan. 25, 2013 for U.S. Appl. No. 11/693,451, filed Mar. 29, 2007 (Inventor—Arthur D. Craig; Applicant—Dignity Health) (pp. 1-13).
Applicant-Initiated Interview Summary issued Feb. 22, 2013 for U.S. Appl. No. 11/693,451, filed Mar. 29, 2007 (Inventor—Arthur D. Craig; Applicant—Dignity Health) (pp. 1-3).

(56) References Cited

OTHER PUBLICATIONS

Supplemental Amendment in Response to Non-Final Office Action filed Mar. 21, 2013 for U.S. Appl. No. 11/693,451, filed Mar. 29, 2007 (Inventor—Arthur D. Craig; Applicant—Dignity Health) (pp. 1-9).
Final Office Action issued May 16, 2013 for U.S. Appl. No. 11/693,451, filed Mar. 29, 2007 (Inventor—Arthur D. Craig; Applicant—Dignity Health) (pp. 1-11).
Amendment in Response to Final Office Action filed Jul. 26, 2013 for U.S. Appl. No. 11/693,451, filed Mar. 29, 2007 (Inventor—Arthur D. Craig; Applicant—Dignity Health) (pp. 1-7).
Supplemental Amendment to Final Office Action filed Aug. 9, 2013 for U.S. Appl. No. 11/693,451, filed Mar. 29, 2007 (Inventor—Arthur D. Craig; Applicant—Dignity Health) (pp. 1-10).
Notice of Allowance issued Aug. 19, 2013 for U.S. Appl. No. 11/693,451, filed Mar. 29, 2007 (Inventor—Arthur D. Craig; Applicant—Dignity Health) (pp. 1-6).
Issue Notification issued Dec. 4, 2013 for U.S. Appl. No. 11/693,451, filed Mar. 29, 2007 (Inventor—Arthur D. Craig; Applicant—Dignity Health) (pp. 1-1).
Non-Final Office Action issued Dec. 2, 2011 for U.S. Appl. No. 12/400,970, filed Mar. 10, 2009 (Inventor—Arthur D. Craig; Applicant—Dignity Health) (pp. 1-15).
Amendment and Response to Office Action received Apr. 2, 2012 for U.S. Appl. No. 12/400,970, filed Mar. 10, 2009 (Inventor—Arthur D. Craig; Applicant—Dignity Health) (pp. 1-21).
Final Office Action isued Jul. 16, 2012 for U.S. Appl. No. 12/400,970, filed Mar. 10, 2009 (Inventor—Arthur D. Craig; Applicant—Dignity Health) (pp. 1-18).
Amendment and Response filed Jan. 16, 2013 for U.S. Appl. No. 12/400,970, filed Mar. 10, 2009 (Inventor—Arthur D. Craig; Applicant—Dignity Health) (pp. 1-13).
Request for Continued Examination filed Jan. 16, 2013 for U.S. Appl. No. 12/400,970, filed Mar. 10, 2009 (Inventor—Arthur D. Craig; Applicant—Dignity Health) (pp. 1-3).
Applicant Initiated Interview Summary issued Feb. 25, 2013 for U.S. Appl. No. 12/400,970, filed Mar. 10, 2009 (Inventor—Arthur D. Craig; Applicant—Dignity Health) (pp. 1-3).
Supplemental Amendment in Response to Final Office Action filed Mar. 21, 2013 for U.S. Appl. No. 12/400,970, filed Mar. 10, 2009 (Inventor—Arthur D. Craig; Applicant—Dignity Health) (pp. 1-10).
Non-Final Office Action issued Mar. 28, 2013 for U.S. Appl. No. 12/400,970, filed Mar. 10, 2009 (Inventor—Arthur D. Craig; Applicant—Dignity Health) (pp. 1-12).
Amendment in Response to Office Action filed Jun. 14, 2013 for U.S. Appl. No. 12/400,970, filed Mar. 10, 2009 (Inventor—Arthur D. Craig; Applicant—Dignity Health) (pp. 1-8).
Examiner Initiated Interview Summary issued Oct. 10, 2013 for U.S. Appl. No. 12/400,970, filed Mar. 10, 2009 (Inventor—Arthur D. Craig; Applicant—Dignity Health) (pp. 1-1).
Notice of Allowance issued Oct. 10, 2013 for U.S. Appl. No. 12/400,970, filed Mar. 10, 2009 (Inventor—Arthur D. Craig; Applicant—Dignity Health) (pp. 1-9).
Issue Notification issued Feb. 5, 2014 for U.S. Appl. No. 12/400,970, filed Mar. 10, 2009 (Inventor—Arthur D. Craig; Applicant—Dignity Health) (pp. 1-1).
Preliminary Amendment filed Nov. 25, 2013 for U.S. Appl. No. 14/089,185, filed Nov. 25, 2013 (Inventor—Arthur D. Craig; Applicant—Dignity Health) (pp. 1-6).
Preliminary Amendment filed Feb. 18, 2014 for U.S. Appl. No. 14/089,185, filed Nov. 25, 2013 (Inventor—Arthur D. Craig; Applicant—Dignity Health) (pp. 1-44).

* cited by examiner

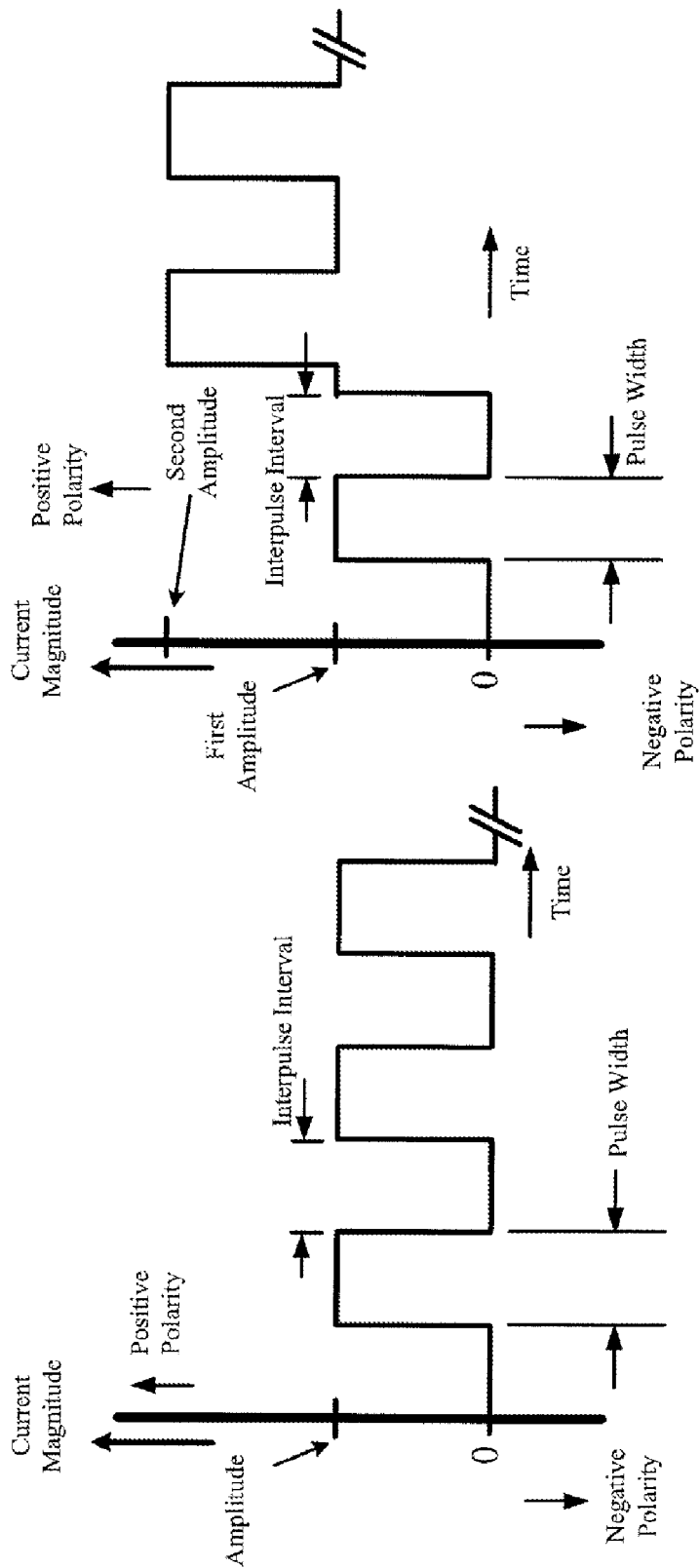

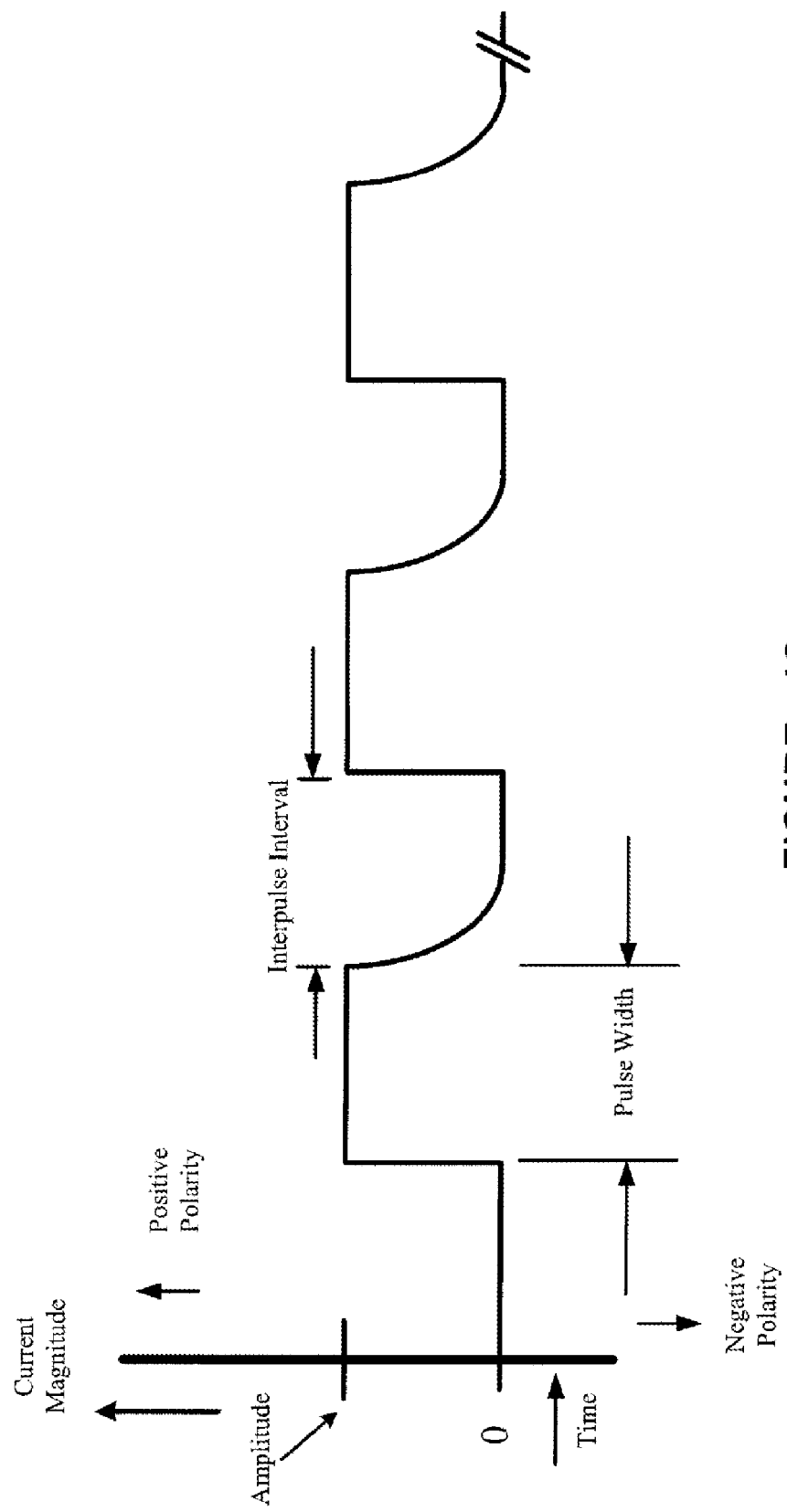

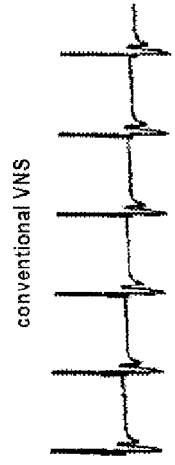
FIGURE 8B
single pulse at 30 Hz (pulse every 33 msec)
conventional VNS
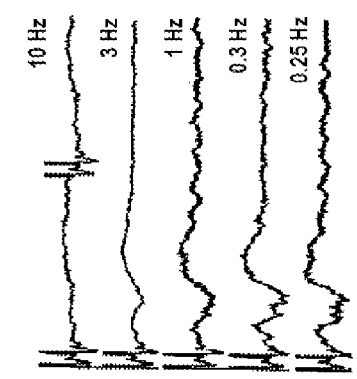
FIGURE 8E
effect of burst frequency
(2 pulses at 6.7 msec interval)
10 Hz, 3 Hz, 1 Hz, 0.3 Hz, 0.25 Hz
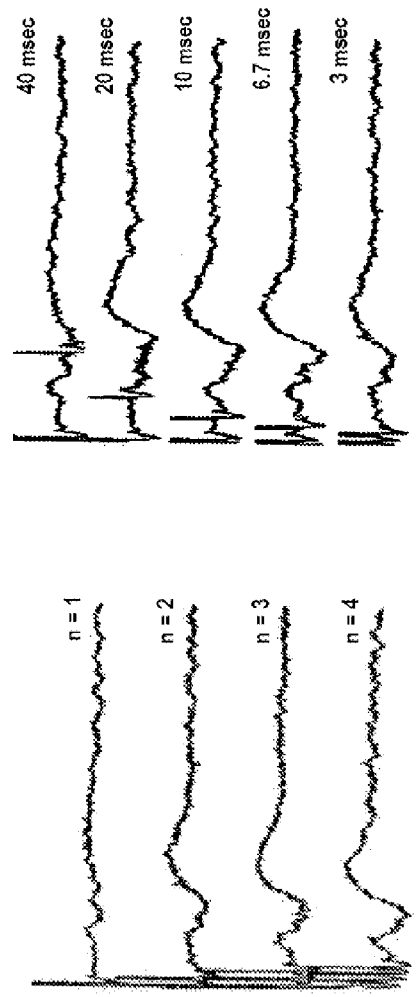
FIGURE 8D
effect of interval between pulses
(every 4 sec)
40 msec, 20 msec, 10 msec, 6.7 msec, 3 msec
FIGURE 8A
single pulse (every 4 sec)
FIGURE 8C
effect of burst duration (number of pulses)
(3 msec interval; every 4 sec)
n = 1, n = 2, n = 3, n = 4

MICROBURST ELECTRICAL STIMULATION OF CRANIAL NERVES FOR THE TREATMENT OF MEDICAL CONDITIONS

CROSS-REFERENCE TO RELATED APPLICATIONS

This application is a continuation of U.S. patent application Ser. No. 12/400,970 (Now U.S. Pat. No. 8,660,666), filed Mar. 10, 2009, which is a continuation of U.S. Pat. No. 8,615,309, filed Mar. 29, 2007, entitled "Microburst Electrical Stimulation of Cranial Nerves for the Treatment of Medical Conditions," which claims priority to U.S. Provisional Patent Application No. 60/787,680, filed Mar. 29, 2006, entitled "Synchronized And Optimized Vagus Nerve Stimulation Method," which applications are hereby incorporated by reference herein in their entirety.

BACKGROUND OF THE INVENTION

1. Field of the Invention

This invention relates generally to medical device systems and, more particularly, to medical device systems for applying electrical signals to a cranial nerve for the treatment of various medical conditions, and for improved electrical signals in such systems.

2. Description of the Related Art

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electromagnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuroplasticity or neurogenesis of brain tissue.

In some embodiments, electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation schemes have been proposed, conventional vagus nerve stimulation (VNS) usually involves non-feedback stimulation characterized by a number of parameters. Specifically, conventional vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-60 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to the vagus nerve 127. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation for this purpose. For example, it may be desirable to enhance evoked potentials in the patient's brain to aid in treating a medical condition.

SUMMARY OF THE INVENTION

Applicant has discovered that it is possible to provide improved therapeutic neurostimulation treatments for a variety of medical conditions by a new type of electrical stimulation of the cranial nerves capable of providing enhanced evoked potentials in the brain. "Enhanced" in this context refers to electrical potentials evoked in the forebrain by neurostimulation that are higher than those produced by conventional neurostimulation, particularly conventional VNS with an interpulse frequency of 20-30 Hz (resulting in a number of pulses per burst of 140-1800, at a burst duration from 7-60 sec). The electrical signal for this improved therapy is substantially different from the electrical signals in conventional VNS. In particular, electrical signals in the present invention are characterized by very short bursts of a limited number of electrical pulses. These shorts bursts of less than 1 second are referred to hereinafter as "microbursts," and electrical stimulation applying microbursts to a cranial nerve is referred to as "microburst stimulation." By applying an electrical signal comprising a series of microbursts to, for example, a vagus nerve of a patient, enhanced vagal evoked potentials (eVEP) are produced in therapeutically significant areas of the brain. Significantly, eVEP are not produced by conventional vagus nerve stimulation.

As used herein, the term "microburst" refers to a portion of a therapeutic electrical signal comprising a limited plurality of pulses and a limited duration. More particularly, in one embodiment, a microburst may comprise at least two but no more than about 25 electrical pulses, preferably from 2 to about 20 pulses per burst, more preferably from 2 to about 15 pulses per burst. In one embodiment, a microburst may last for no more than 1 second, typically less than 100 milliseconds, and preferably from about 10 msec to about 80 msec. A therapeutic electrical signal may comprise a series of microbursts separated from one another by time intervals known as "interburst periods" which allow a refractory interval for the nerve to recover from the microburst and again become receptive to eVEP stimulation by another microburst. In some embodiments, the interburst period may be as long as or longer than the adjacent microbursts separated by the interburst period. In some embodiments the interburst period may comprise an absolute time period of at least 100 milliseconds. Adjacent pulses in a microburst are separated by a time interval known as an "interpulse interval." The interpulse interval, together with the number of pulses and the pulse width of each pulse, determines a "microburst duration," which is the length of a microburst from the beginning of the first pulse to the end of the last pulse (and thus the beginning of a new interburst period). In one embodiment, a microburst may have a microburst duration of 1.0 seconds or less (i.e., not greater than 1 sec), such as from about 2 msec to about 1 sec, and more preferably 100 msec or less, such as from about 5 msec to about 100 msec, and more preferably from about 10 msec to about 80 msec. The improved electrical signals of the present invention are thus characterized by an interburst period, a microburst duration, a number of pulses per microburst, and an interpulse interval. The pulses in a microburst may be further characterized by a current amplitude and a pulse width. Electrical stimulation according to the present invention may optionally include an on-time and an off-time in which the microbursts are provided and not provided, respectively, to a cranial nerve. At least one of the interburst period, the burst duration, the number of pulses per microburst, the interpulse interval, the current amplitude, the pulse width, the on-time, or the off-time can be selected to enhance cranial nerve evoked potentials.

In one embodiment, the present invention provides a method of treating a patient having a medical condition by applying a pulsed electrical signal comprising a series of microbursts, wherein each of said microbursts has at least one characteristic selected from the group consisting of having from 2 pulses to about 25 pulses per microburst, having an interpulse interval of about 1 millisecond to about 50 milliseconds (such as from about 1 msec to about 10 msec), having a microburst duration of less than 1 sec, and being separated from an adjacent microburst by an interburst period comprising a time interval selected from the group consisting of A) the microburst duration or the microburst duration of the adjacent microburst and B) at least 100 milliseconds.

In one embodiment, the present invention provides a method of treating a medical condition of a patient with an electrical signal from an implantable medical device, comprising applying to a cranial nerve of a patient a pulsed electrical signal comprising a series of microbursts separated by interburst periods. Each microburst comprises a number of pulses per microburst, an interpulse interval, and a microburst duration. The microbursts are applied to a portion of a cranial nerve of said patient, wherein at least one of the interburst period, the microburst duration, the number of pulses per microburst, or the interpulse interval is selected to enhance cranial nerve evoked potentials.

In one embodiment, the present invention provides a method of treating a medical condition of a patient, comprising coupling at least one electrode to at least one cranial nerve of the patient, providing a programmable electrical signal generator coupled to the electrode, and generating a pulsed electrical signal comprising a series of microbursts separated by interburst periods. Each microburst comprises a number of pulses per microburst and an interpulse interval and has a microburst duration. The method further comprises selecting at least one of the interburst period, the number of pulses per microburst, the microburst duration, or the interpulse interval to enhance cranial nerve evoked potentials, and applying the pulsed electrical signal to the at least one electrode to treat the medical condition.

In one embodiment, the present invention provides a computer readable program storage device encoded with instructions that, when executed by a computer, perform a method, comprising generating an electrical signal comprising a series of microbursts separated by interburst periods, with each microburst comprising a number of pulses per microburst, an interpulse interval, and a microburst duration, wherein at least one of the interburst period, the number of pulses per microburst, the microburst duration, or the interpulse period is selected to enhance cranial nerve evoked potentials, and applying the electrical signal to a cranial nerve of the patient to treat the medical condition.

In one embodiment, the present invention provides a system for treating a medical condition of a patient, comprising at least one electrode coupled to at least one cranial nerve of a patient and an implantable device operatively coupled to the electrode and comprising an electrical signal generator capable of generating an electrical signal comprising a series of microbursts separated by interburst periods, with each microburst comprising a number of pulses per microburst, an interpulse interval and a microburst duration, and applying the electrical signal to a portion of a cranial nerve of said patient using the electrode, wherein at least one of the interburst period, the number of pulses per microburst, the interpulse interval or the microburst duration, is selected to enhance cranial nerve evoked potentials.

BRIEF DESCRIPTION OF THE DRAWINGS

The invention may be understood by reference to the following description taken in conjunction with the accompanying drawings, in which like reference numerals identify like elements, and in which:

FIGS. 4A, 4B, and 4C illustrate exemplary waveforms for electrical signals for stimulating the cranial nerve for treating a medical condition, according to one illustrative embodiment of the present invention;

FIGS. 8A-8E show a comparison of vagal evoked potentials (VEPs) with different stimulus timings;

Figure 1:
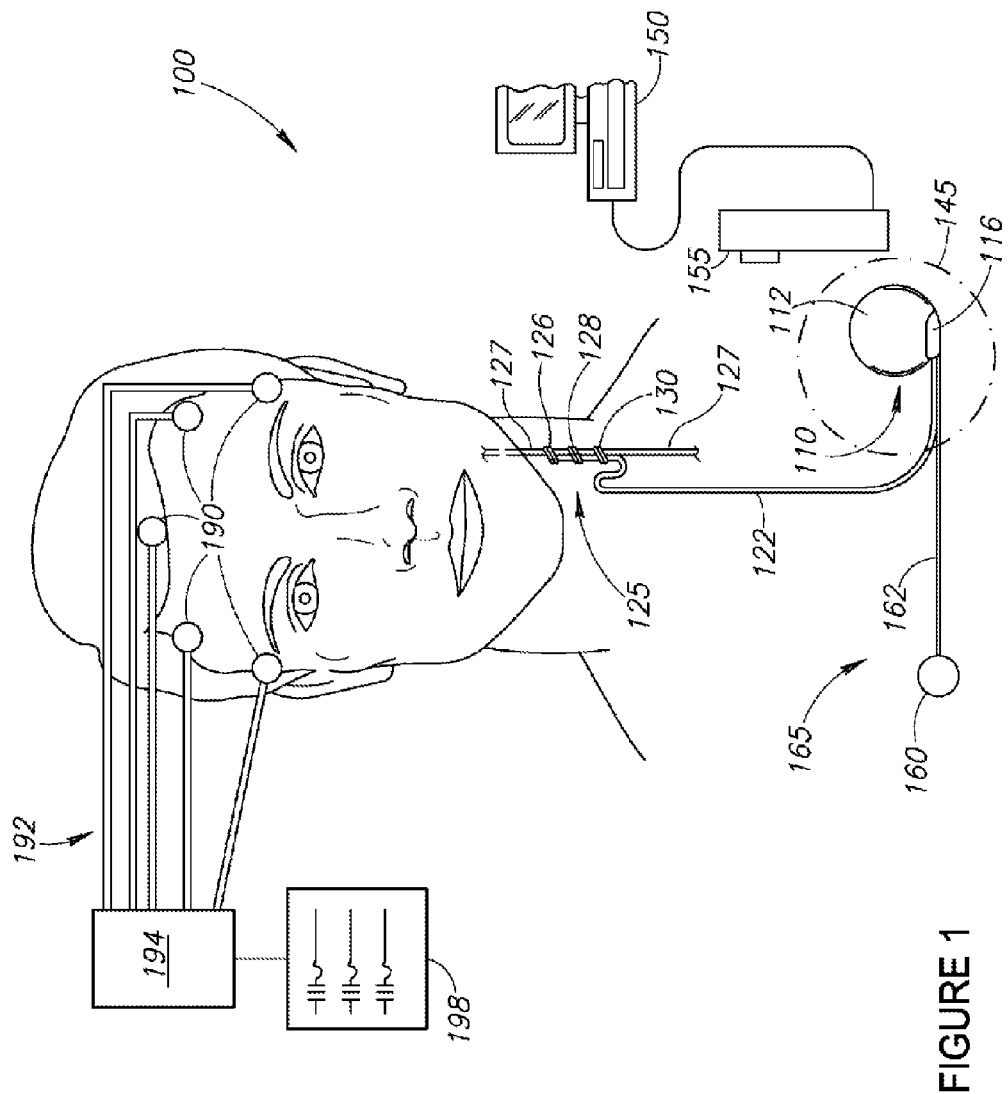
FIG. 1 provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present invention provides a method of treating a medical condition. The medical condition can be selected from the group consisting of epilepsy, neuropsychiatric disorders (including but not limited to depression), eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including infertility).

In one embodiment, the present invention provides a method of treating a medical condition of a patient using an implantable medical device, comprising applying to a cranial nerve of a patient a pulsed electrical signal comprising a series of microbursts separated by interburst periods. In one embodiment, the interburst periods comprise at least 100 milliseconds each. In another embodiment, the interburst periods comprise at least the length of one of the two microbursts separated by the interburst period. In another embodiment, the interburst period may be determined on a particular patient by providing microbursts separated by increasingly smaller interburst periods. The interburst period may be provided as any time interval greater than that at which the eVEP significantly diminishes or disappear. Each microburst comprises a number of pulses per microburst, an interpulse interval, and has a microburst duration. In one embodiment, the number of pulses per microburst may range from 2 to about 25 pulses, and in another embodiment the number pulses per microburst may range from 2 to about 20 pulses, preferably from 2 to about 15 pulses. The microbursts are applied to a portion of a cranial nerve of the patient, and at least one of the interburst period, the number of pulses per microburst, the interpulse interval, or the microburst duration are selected to enhance cranial nerve evoked potentials. Pulses within a microburst may also comprise a pulse width and a current amplitude. In an alternate embodiment, the method may also comprise an off-time, during which microbursts are not applied to the patient, and an on-time during which microbursts are applied to the patient.

It may be convenient to refer to a burst frequency, defined as 1 divided by the sum of the microburst duration and the interburst period, and it will be recognized by persons of skill in the art that the interburst period may alternatively be described in terms of a frequency of the pulses rather than as an absolute time separate one pulse from another.

In another alternate embodiment, the method may comprise, during a first period, applying a primary mode of cranial nerve stimulation to a cranial nerve of the patient, such as conventional vagus nerve stimulation, and, during a second period, applying a secondary mode of cranial nerve stimulation to a cranial nerve of the patient, such as microburst stimulation. The conventional vagus nerve stimulation signal may be defined by a current amplitude, a pulse width, a frequency, an on-time and an off-time. The conventional vagus nerve stimulation signal typically has more than about 50 pulses per burst and a burst duration of at least about 7 sec. In one embodiment, the first period corresponds to the on-time of conventional vagus nerve stimulation and the second time period corresponds to the off-time of conventional vagus nerve stimulation. In another embodiment, the first period and the second period can partially overlap. In another embodiment, one of the first period or the second period can be entirely overlapped by the other of the first period or the second period.

The implantable medical device (IMD) system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define the therapeutic electrical signals delivered by the IMD, medication parameters and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, an interburst period, a number of pulses per burst, an interpulse interval, a burst duration, an on-time, and an off-time.

Although not so limited, a system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed to trigger active stimulation. Both passive and active stimulation may be combined or delivered by a single IMD according to the present invention. Either or both modes may be appropriate to treat a specific patient under observation.

In alternative embodiments, a sensor assembly 165, comprising a sensor lead assembly 162 and a sensor 160, may be employed to detect a body parameter of the patient.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The therapeutic electrical stimulation signal described herein may be used to treat a medical condition by enhancing cranial nerve evoked potentials separately, or in combination with another type of treatment. For example, electrical signals according to the present invention may be applied in combination with a chemical agent, such as various drugs, to treat various medical conditions. Further, the electrical stimulation may be performed in combination with treatment(s) relating to a biological or chemical agent. The electrical stimulation treatment may also be performed in combination with other types of treatment, such as magnetic stimulation treatment.

Figure 2:
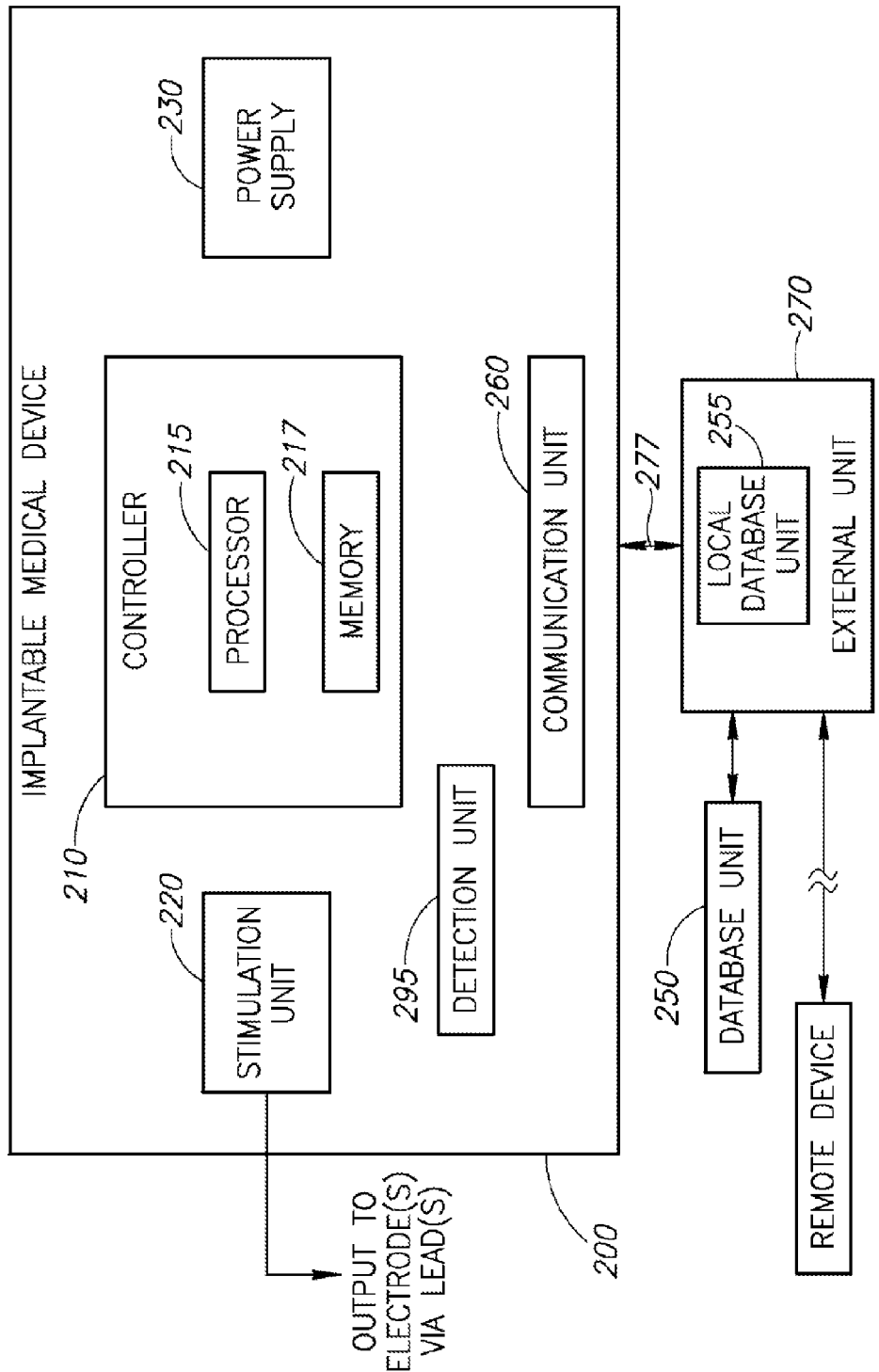
FIG. 2 is a block diagram of a medical device system that includes an implantable medical device and an external device, in accordance with one illustrative embodiment of the present invention.

Turning now to FIG. 2, a block diagram depiction of the IMD 200 is provided, in accordance with one illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering an electrical signal over the leads comprising the lead assembly 122.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCF$_x$) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 that may comprise an ED (FIG. 1). The communication unit 260 may include hardware, software, firmware, or any combination thereof.

In one embodiment, the IMD 200 may also comprise a detection unit 295 that is capable of detecting various patient parameters. For example, the detection unit 295 may comprise hardware, software, or firmware that is capable of obtaining and/or analyzing data relating to one or more body parameters of the patient. Based upon the data obtained by the detection unit 295, the IMD 200 may deliver the electrical signal to a portion of the cranial nerve to treat epilepsy, depression or other medical conditions. In one embodiment, the detection unit 295 may be capable of detecting a feedback response from the patient. The feedback response may include a magnetic signal input, a tap input, a wireless data input to the MID 200, etc. The feedback may be indicative of a pain and/or noxious threshold, wherein the threshold may be the limit of tolerance of discomfort for a particular patient. The term "patient parameters" may refer to, but is not limited to, various body parameters, which may in some embodiments involve sensors coupled to the IMD 200.

In another embodiment, the detection unit 295 may comprise hardware, software, or firmware that is capable of obtaining and/or analyzing data relating to one or more body parameters of the patient's cardiac cycle. Based upon the data obtained by the detection unit 295, the IMD 200 may deliver the electrical signal to a portion of the cranial nerve to treat epilepsy, depression or other medical conditions.

The external unit 270 may be an ED that is capable of programming electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider.

Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may download various parameters and program software into the MD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIG. 2. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions using the external unit 270, which may include obtaining and/or analyzing data from the IMD 200 and/or data from the database unit 250 and/or the local database unit 255. The database unit 250 and/or the local database unit 255 may store various patient data.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
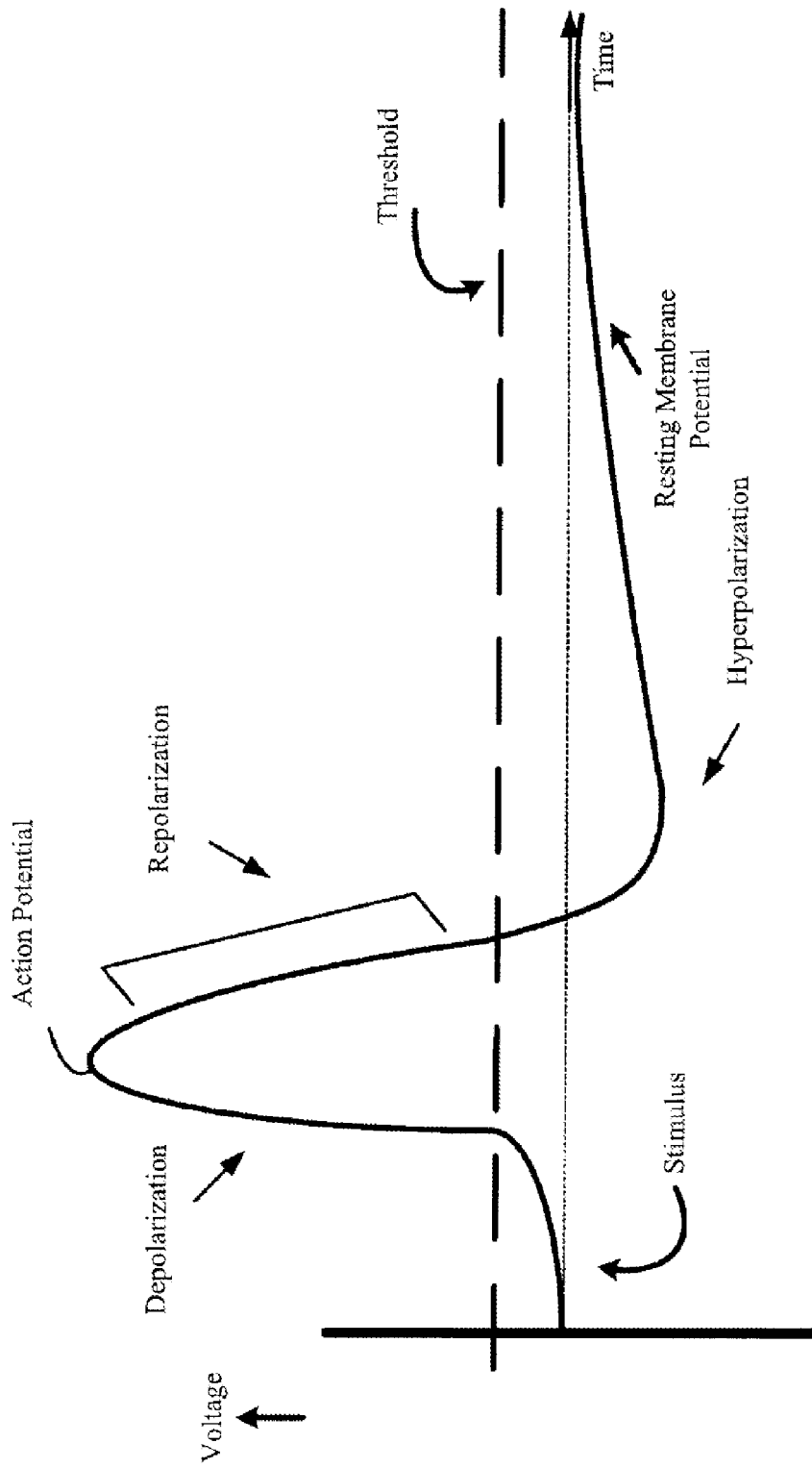
FIG. 3 illustrates an exemplary electrical signal of a firing neuron as a graph of voltage at a given location at particular times in response to application of an electrical signal to the nerve by the neurostimulator of FIG. 2, in accordance with one illustrative embodiment of the present invention.

FIG. 3 provides a stylized depiction of an exemplary electrical signal of a firing neuron as a graph of voltage at a given point on the nerve at particular times during the propagation of an action potential along the nerve, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur.

Referring again to FIG. 1, the IMD 100 may generate a pulsed electrical signal in embodiments of the present invention for application to a cranial nerve such as vagus nerve 127 according to one or more programmed parameters. In one embodiment, the parameters defining the electrical signal may be selected from the group consisting of an interburst period, a number of pulses per burst, an interpulse interval, a burst duration, a current magnitude, a pulse width, an on-time, and an off-time. Suitable ranges for these parameters may comprise a variety of values. In particular, the interburst period in microburst signals according to the present invention may, in one embodiment, be 100 milliseconds or greater, preferably 100 milliseconds to 10 minutes, and more preferably 1 second to 5 seconds. In another embodiment, the interburst period may be equal to or greater than the microburst duration of one of the two adjacent microbursts that the interburst period separates. The number of pulses comprising a microburst may range from about 2 to about 25 pulses, such as from 2 to about 20 pulses, and more specifically from 2 to about 15 pulses. Suitable interpulse intervals in the present invention may range from about 1 millisecond to about 50 milliseconds, more preferably from about 2 milliseconds to about 10 milliseconds. Suitable microburst durations may range from about 2 msec to about 1 sec, preferably less than about 100 msec, more preferably from about 5 msec to about 100 msec, and even more preferably from about 10 msec to about 80 msec.

Ranges for current magnitude and pulse width may comprise values similar to those for conventional VNS signals, e.g., current magnitudes of 0.10-6.0 milliamps, preferably 0.25-3.0 milliamps, and more preferably 0.5-2.0 milliamps. Pulse widths may range from about 0.05 to about 1.0 milliseconds, preferably 0.25 to about 0.5 milliseconds. In view of the stated values of pulse width and interpulse intervals, a 2-pulse microburst could comprise a microburst duration of as little as 1.1 milliseconds, while a microburst of 25 pulses could last as long as about 1275 milliseconds, although microburst durations of 100 milliseconds or less are preferred. In embodiments of the present invention, however, the microbursts are no greater than 1 second in duration.

In one embodiment, microburst signals of the present invention may be applied to the nerve continuously, with microbursts being applied to the nerve separated only by the interburst period (e.g., 1 to 5 seconds in a preferred embodiment). In an alternative embodiment, the concepts of "on-time" and "off-time" associated with conventional VNS therapy may be used to provide an on-time interval in which microbursts, separated by the interburst period, are applied to the nerve for the duration of the on-time, followed by an off-time period in which no electrical signal is applied to the nerve. Thus, for example, a series of microbursts separated by an interburst period of 1 second, in which each microburst comprises 3 pulses separated by an interpulse interval of 5 msec, may be applied to a vagus nerve of the patient for an on-time of 5 minutes, followed by an off-time of 10 minutes in which no electrical signal is applied to the nerve. In some embodiments, the on-time may range from about 100 msec to about 60 minutes. In such embodiments, the off-times may range from 200 msec to 24 hours or more.

In a further embodiment, during the off-time of the microburst stimulation, an alternative stimulation technique, such as conventional cranial nerve stimulation, can be performed. Conventional cranial nerve stimulation generally also involves an on-time and an off-time, and the on-time of the microburst stimulation may be during the off-time of the conventional cranial nerve stimulation.

If both microburst stimulation and an alternative stimulation technique are performed, the on-times, the off-times, or both of the two stimulation regimes may partially or wholly overlap.

Exemplary pulse waveforms in accordance with one embodiment of the present invention are shown in FIGS. 4A-4C. Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

In microburst stimulation according to the present invention, the microbursts are markedly shorter in both the number of pulses and the microburst duration compared to pulse bursts in conventional neurostimulation such as vagus nerve stimulation. While conventional VNS typically involves pulse bursts at a frequency of 20-30 Hz for a period of from 7-60 seconds (resulting in a burst having from 140-1800 pulses or more), microbursts according to the present invention, by contrast, can have a microburst duration from about 1 msec to no more than 1 second. Further, each microburst comprises at least 2 and about 25 pulses, with each of the pulses separated from an adjacent pulse by an interpulse interval of from about 1 to about 50 milliseconds, more typically from about 2 to about 10 milliseconds. While the individual pulses in a microburst according to this aspect of the invention may resemble conventional VNS signal pulses in pulse width and pulse current, the number of pulses in a microburst is markedly smaller than in a pulse burst in conventional VNS therapy. Consequently, microbursts are also much shorter in duration (less than 1 second and typically less than 100 msec, such as from about 10 msec to about 80 msec) than pulse bursts in conventional neurostimulation therapy (at least 7 seconds and typically 20-60 seconds). Moreover, in most cases, the interpulse interval separating the pulses is shorter than in conventional neurostimulation (typically 2-10 msec for microbursts compared to 30-50 msec for conventional VNS). Pulse bursts of the present invention are termed "microbursts" because they are significantly shorter in both the number of pulses and the total microburst duration than conventional neurostimulation signals.

As noted, it has been discovered by the present inventor that microbursts according to this aspect of the invention are capable of providing an enhanced vagal evoked potential (eVEP) in the patient's brain that is significantly greater than VEPs produced by conventional vagus nerve stimulation signals. This eVEP is attenuated, however, as the number of pulses increases beyond an optimal number of pulses. Thus, for example, in the monkey model discussed below, where a microburst exceeds 2-5 pulses, the eVEP begins to diminish, and if more than 15 pulses are provided, the eVEP is highly diminished. To maintain the eVEP effect, this aspect of the present invention requires a small number of pulses in a microburst as well as an interburst period separating each microburst from the adjacent microburst in order to allow the nerve a refractory space to recover from the microburst. Providing an appropriate interburst period ensures that the succeeding microburst in the electrical signal is capable of generating an eVEP. In one embodiment the interburst period is as long as or longer than the duration of the adjacent microbursts separated by the interburst period. In another embodiment, the interburst period is at least 100 milliseconds, such as from about 1 sec to about 5 sec. Each microburst comprises a series of pulses that, in some embodiments, are intended to mimic the endogenous afferent activity on the vagus nerve. In one embodiment the microbursts may simulate afferent vagal action potentials associated with each cardiac and respiratory cycle.

Although evoked potentials have been discussed above in the context of the vagus nerve, enhanced evoked potentials can be generated by microburst stimulation of any cranial nerve, e.g. the trigeminal nerve or glossopharyngeal nerve, and remain within the spirit and scope of the present invention. Thus, while the present invention is presented, in certain embodiments, as providing microburst stimulation to a vagus nerve of a patient, microburst stimulation may also be applied to other cranial nerves, and particularly the trigeminal nerve and the glossopharyngeal nerve.

The central vagal afferent pathways involve two or more synapses before producing activity in the forebrain. Each synaptic transfer is a potential site of facilitation and a nonlinear temporal filter, for which the sequence of interpulse intervals in a microburst can be optimized. Without being bound by theory, it is believed that the use of microbursts enhances VNS efficacy by augmenting synaptic facilitation and "tuning" the input stimulus train to maximize the forebrain evoked potential.

For example, as shown in FIG. 8, the vagal evoked potential (VEP) measured in the monkey thalamus is barely visible if elicited by a single stimulus pulse on the vagus nerve (FIG. 8A) and it virtually disappears if the single stimuli are presented in a train at 30 Hz, as in conventional neurostimulation (FIG. 8B). However, as shown in the series of traces in the middle and lower panels of the figure, the VEP is enormously enhanced (resulting in eVEP) and optimized by using a microburst of pulses (2-6 pulses, microburst duration ltoreq.1 second, FIG. 8C) at appropriate interpulse intervals (in this case, 6.7 msec was optimal for the first interpulse interval, shown in FIG. 8D) and at an interburst period (i.e., burst frequency) that approximates the electrocardiogram R-R cycle (the period between R-waves of consecutive heartbeats) in the monkey (in this case 0.3 Hz, shown as FIG. 8E).

The use of pairs of pulses is a standard physiological tool for producing central responses by stimulation of small-diameter afferent fibers. However, according to the present disclosure, a microburst with an appropriate sequence of interpulse intervals enormously enhances the effect of neurostimulation. By selecting an appropriate interburst period, an electrical signal for neurostimulation may comprise a series of microbursts that each provide eVEP. As illustrated in FIG. 8, a microburst duration of >10 msec produces a maximal VEP in the monkey and a first interpulse interval of .about.6-9 msec produces maximal facilitation, and so according to the present disclosure, a microburst of pulses with a total duration of about 10-20 msec and with an interpulse interval of about 6-9 msec and subsequent microbursts of similar duration will produce an optimal VEP in the monkey model. Though not to be bound by theory, the eVEP may result because such a microburst simulates the pattern of action potentials that occur naturally in the small-diameter afferent vagal fibers that elicit the central response that the present enhanced and optimized therapy may evoke (see below). Selection of an appropriate interburst period to separate one microburst from the next may be performed experimentally, although as previously noted, a refractory period of at least 100 msec (such as from 100 msec to 10 min, such as 1 sec to 5 sec) and at least equal to the microburst duration is most desired.

Figure 9:
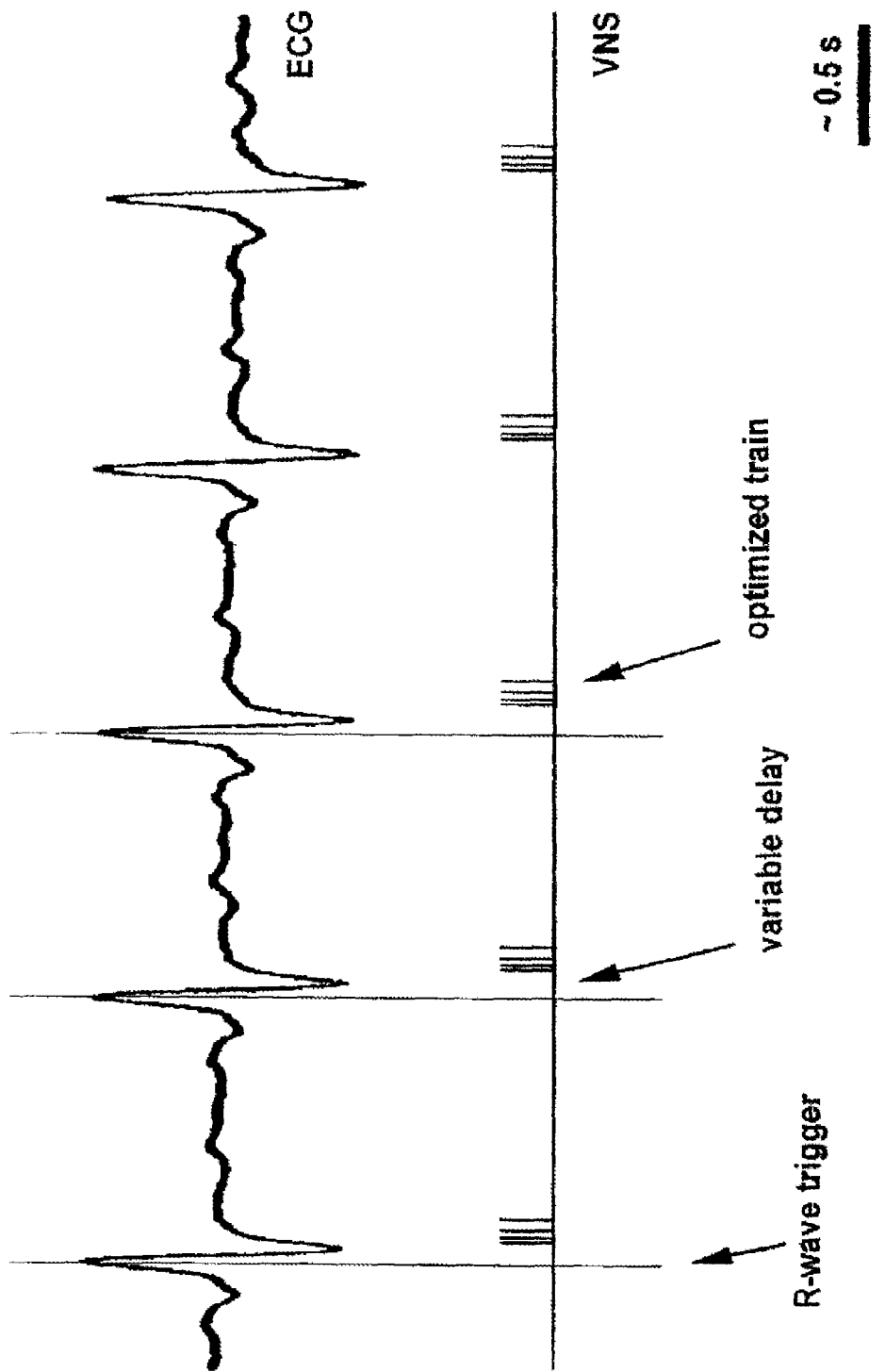
FIG. 9 illustrates synchronization of a vagal stimulus burst to the QRS wave of a patient's ECG.

The sequence of interpulse intervals may vary with the patient's heart rate variability (HRV) (reflecting cardiac and respiratory timing) and also between individual patients, and thus, in one embodiment, the number of pulses, on-time duration, off-time duration, microburst frequency, the interpulse interval, the interburst period, and the microburst duration may be optimized for each patient. As a standard microburst sequence for initial usage, a microburst of 2 or 3 pulses at interpulse intervals of 5-10 msec will approximate the short peak of endogenous post-cardiac activity. The interburst period may also be determined empirically by providing microbursts with a steadily decreasing interburst period until the eVEP begins to decline. In one embodiment, the interpulse interval is a series of equal intervals (i.e., the simplest train) or increasing intervals, simulating the pattern of a decelerating post-synaptic potential, as illustrated in FIG. 9. In an alternative embodiment, the interpulse intervals may decrease through the microburst, or may be randomly determined within a preselected range, e.g., 5-20 msec. This modification of conventional neurostimulation methodology may produce a significant enhancement of neurostimulation efficacy that is applicable to many different medical conditions.

The optimization may be accomplished by recording, using surface electrodes, a far-field VEP, which originates from the thalamus and other regions of the forebrain, and varying the stimulus parameters in order to maximize the recorded potential. As illustrated in FIG. 1, standard EEG recording equipment 194 and 16- or 25-lead electrode placement (of which five electrodes 190 are shown, with leads 192 in electrical communication with the EEG recording equipment 194), such as typically used clinically for recording somatosensory or auditory evoked potentials, will enable the VEP to be recorded and identified as an EEG recording 198. Neurostimulation stimulus burst timing can be used to synchronize averages of 8 to 12 epochs, if desired. By testing the effects of varied numbers of pulses, interpulse intervals, microburst durations, and interburst periods in defining the microbursts, the peak-to-peak amplitude of the eVFP in a microburst can be optimized in each patient.

Neurostimulation can be optimized in individual patients by selected stimulus parameters that produce the greatest effect as measured with EEG surface electrodes. The current amplitude and pulse width is first optimized by measuring the size of the VEP elicited by individual pulses (as opposed to a microburst). The number of pulses, interpulse intervals, microburst durations, and interburst periods for the microbursts are then optimized using the current amplitude and pulse width previously determined, by measuring the size of the eVEP induced by the microbursts.

Because the large eVEPs recorded in the thalamus, striatum, and insular cortex of the anesthetized monkey shown in FIG. 8, are large enough that if evoked in a human patient, the eVEPs are observable in a standard EEG detected using electrodes adjacent to the human patient's scalp, the standard EEG may be used to indicate the effects of modifications to the signal parameters of the exogenous electrical signal. In this manner, the EEG may be used to optimize or tune the neurostimulation electrical signal parameters for microbursts empirically. Without being bound by theory, it is believed that the eVEP recorded in the right thalamus and striatum is significant for the anti-epileptic effects of neurostimulation, whereas another potential (in the left insular cortex) is most significant for the anti-depression effects of neurostimulation. By using regional EEG localization on the right or left frontal electrodes (FIG. 10), the neurostimulation electrical signal parameters for microbursts according to this aspect of the invention can be optimized appropriately by measuring the eVEP in these respective regions for individual patients.

The optimal microburst parameters for eliciting eVEPs from these two areas (right thalamus/striatum and left insular cortex, respectively) may differ. Both eVEPs are identifiable with EEG recording methods in awake human patients, so that the appropriate area may easily be used for parametric optimization in an epilepsy or depression patient.

Figure 10:
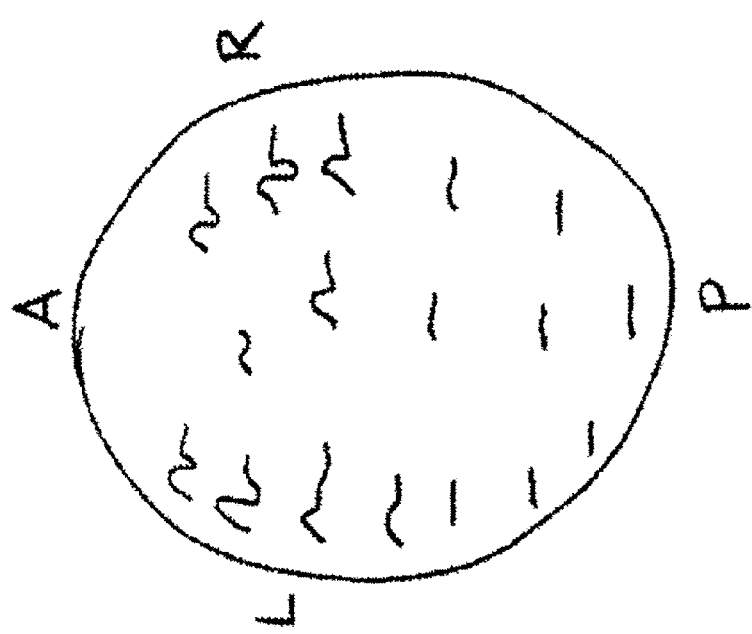
FIG. 10 illustrates the localization of an early VEP in the right thalamus and basal ganglia and a later VEP in the left insular cortex.

The regional EEG localization represented in FIG. 10 allows the early VEP in the right thalamus and basal ganglia associated with the antiepileptic effects of neurostimulation to be distinguished from the later VEP in the left thalamus and insular cortex that may be associated with the treatment of other medical conditions.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the IMD 100 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the cranial nerve, such as vagus nerve 127, and the additional impedance of the skin of the patient. Although external systems typically require greater power consumption than implantable ones, they have an advantage in that their batteries may be replaced without surgery.

Returning to systems for providing cranial nerve stimulation, such as that shown in FIGS. 1 and 2, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the IMD 100 to stimulate the cranial nerve, such as vagus nerve 127, to treat an acute episode of a medical condition. The patient may also be permitted to alter the intensity of the signals applied to the cranial nerve within limits established by the physician.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110. Two taps spaced apart by a slightly longer duration of time may be programmed into the IMD 100 to indicate a desire to deactivate the electrical signal generator 110, for example. The patient may be given limited control over operation of the device to an extent which may be determined by the program dictated or entered by the attending physician. The patient may also activate the IMD 100 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a cardiac cycle sensor. The sensor may also include a nerve sensor for sensing activity on a nerve, such as a cranial nerve, such as the vagus nerve 127.

In one embodiment, the sensor may sense a body parameter that corresponds to a symptom of a medical condition. If the sensor is to be used to detect a symptom of the medical condition, a signal analysis circuit may be incorporated into the IMD 100 for processing and analyzing signals from the sensor. Upon detection of the symptom of the medical condition, the processed digital signal may be supplied to a microprocessor in the IMD 100 to trigger application of the electrical signal to the cranial nerve, such as vagus nerve 127. In another embodiment, the detection of a symptom of interest may trigger a stimulation program including different stimulation parameters from a passive stimulation program. This may entail providing a higher current stimulation signal or providing a higher ratio of on-time to off-time.

Figure 5:
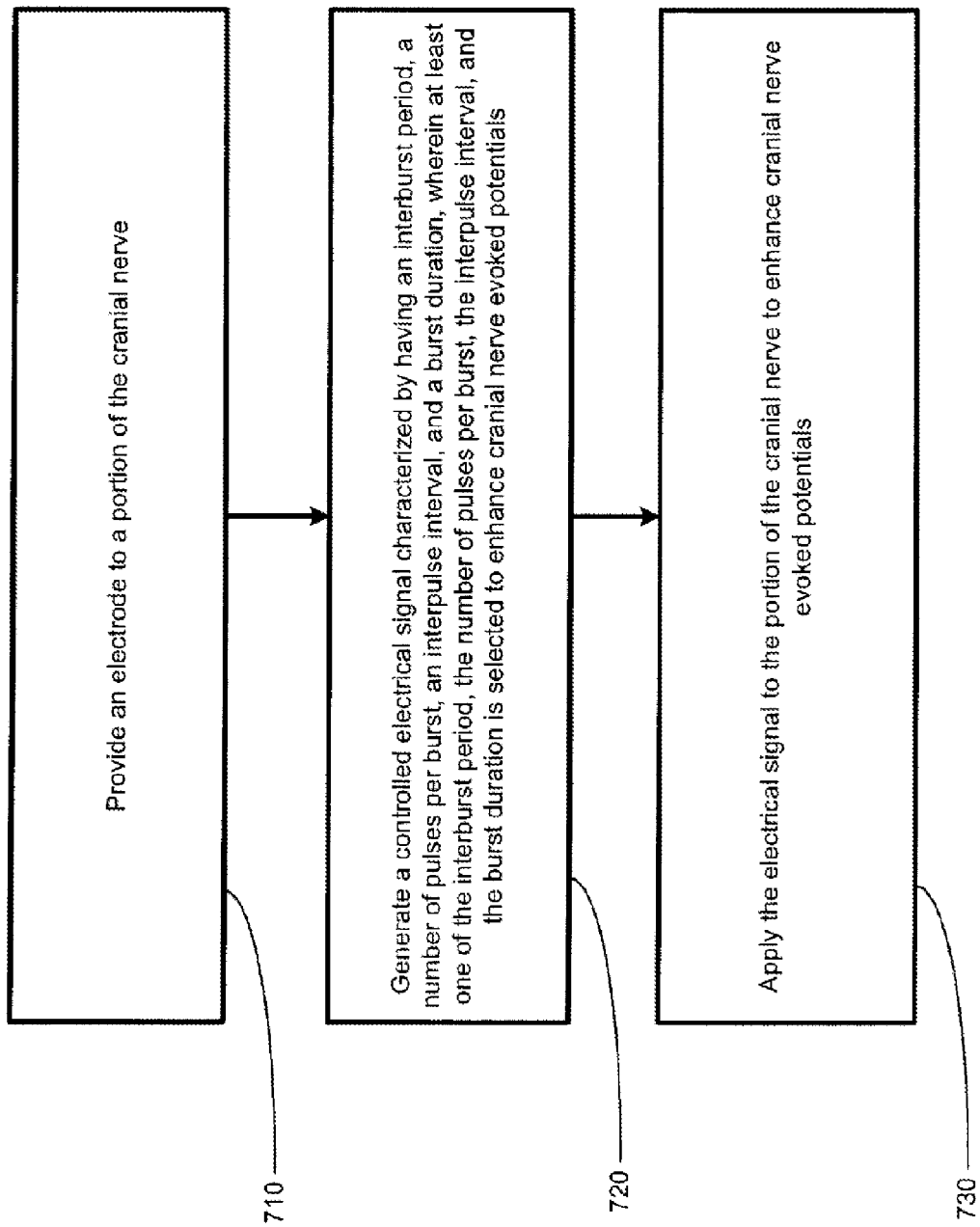
FIG. 5 illustrates a flowchart depiction of a method for treating a medical condition, in accordance with an illustrative embodiment of the present invention.

Turning now to FIG. 5, a flowchart depiction of a method for treating a medical condition, in accordance with one illustrative embodiment of the present invention is provided. An electrode may be coupled to a portion of a cranial nerve to enhance cranial nerve evoked potentials. In one embodiment, one or more electrodes may be positioned in electrical contact or proximate to a portion of the cranial nerve to deliver a stimulation signal to the portion of the cranial nerve (block 710). The electrodes may be operatively coupled to at least one of a main trunk of the right or left vagus nerve, or any branch thereof. The IMD 100 may then generate a controlled electrical signal characterized by an interburst period, a number of pulses per microburst, an interpulse interval, and a microburst duration, wherein at least one of the interburst period, the number of pulses per microburst, the interpulse interval, or the microburst duration is selected to enhance cranial nerve evoked potentials (block 720). This may include a predetermined electrical signal that is pre-programmed based upon a particular condition of a patient. For example, a physician may pre-program the type of stimulation to provide in order to enhance cranial nerve evoked potentials in the patient based upon data specific to the patient. The IMD 100 may then generate a signal, such as a controlled-current microburst signal, to affect one or more portions of the neurological system of a patient.

The IMD 100 may then deliver the stimulation signal to the portion of the cranial nerve (block 730). The application of the electrical signal may be delivered to the main trunk of the right or left vagus nerve, or any branch thereof. In one embodiment, application of the stimulation signal may be designed to promote an afferent effect. Further, the stimulation by the IMD 100 may reduce incidents or symptoms relating to a medical condition.

Additional functions, such as a detection process, may be alternatively employed with the embodiment of the present invention. The detection process may be employed such that an external detection or an internal detection of a bodily function may be used to adjust the operation of the IMD 100.

Figure 6:
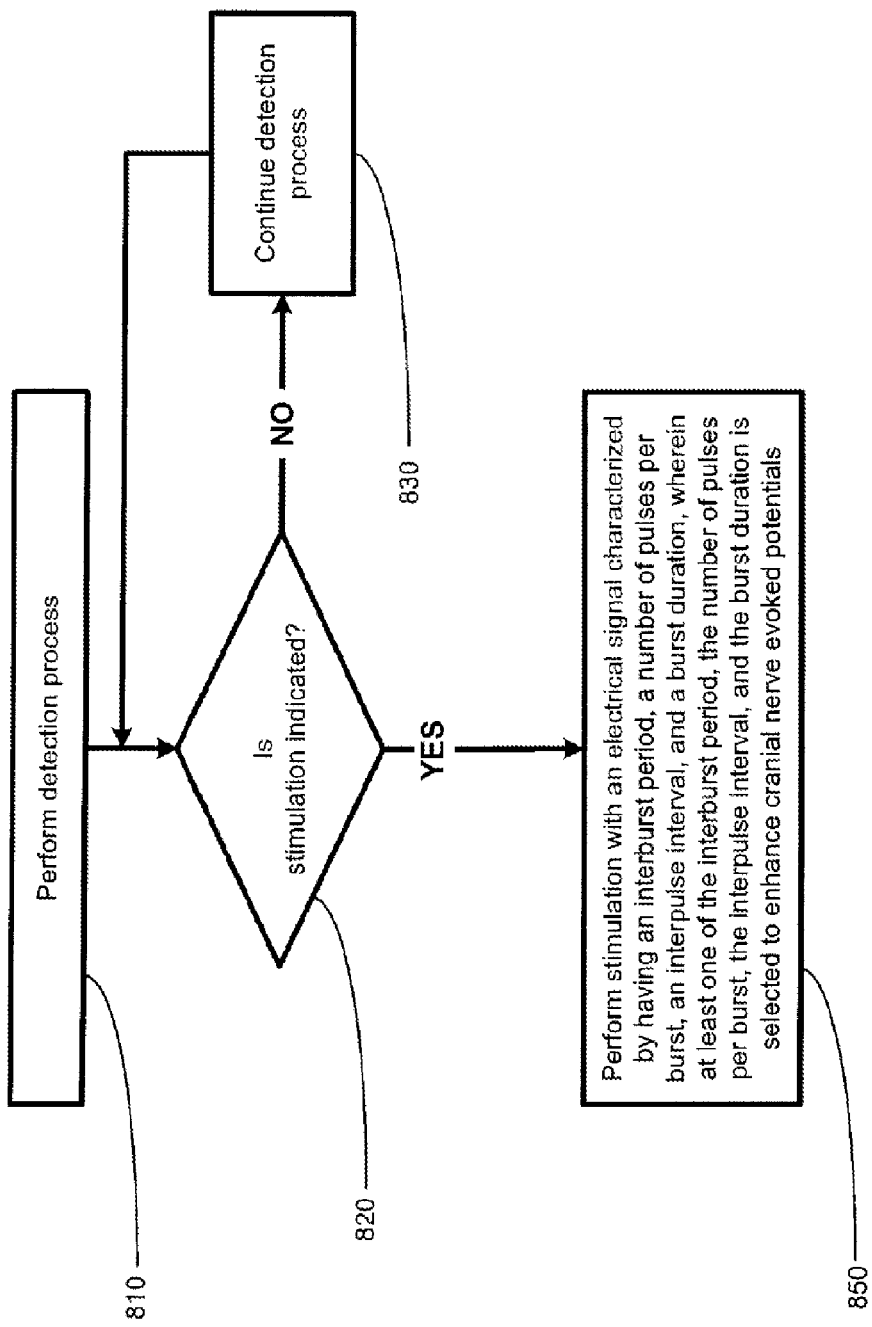
FIG. 6 illustrates a flowchart depiction of an alternative method for treating a medical condition, in accordance with an alternative illustrative embodiment of the present invention.

Turning now to FIG. 6, a block diagram depiction of a method in accordance with an alternative embodiment of the present invention is illustrated. The IMD 100 may perform a database detection process (block 810). The detection process may encompass detecting a variety of types of vital signs or other body parameters of the patient. A more detailed depiction of the steps for performing the detection process is provided in FIG. 7, and accompanying description below. Upon performing the detection process, the IMD 100 may determine if stimulation is indicated (block 820). Upon a determination that stimulation is not indicated, the detection process is continued (block 830).

Upon a determination that stimulation is indicated, a determination as to the type of stimulation based upon data relating to the patient's condition is made (block 840). The type of stimulation may be determined in a variety of manners, such as performing a look-up in a look-up table that may be stored in the memory 217. Alternatively, the type of stimulation may be determined by an input from an external source, such as the external unit 270 or an input from the patient. Further, determination of the type of stimulation may also include determining the location as to where the stimulation is to be delivered. Accordingly, the selection of particular electrodes, which may be used to deliver the stimulation signal, is made.

Upon determining the type of stimulation to be delivered, the IMD 100 performs the stimulation by delivering the electrical signal to one or more selected electrodes (block 850). Upon delivery of the stimulation, the IMD 100 may monitor, store, or compute the results of the stimulation (block 860). For example, based upon the calculation, a determination may be made that adjustment(s) to the type of signal to be delivered for stimulation, may be performed. Further, the calculations may reflect the need to deliver additional stimulation. Additionally, data relating to the results of stimulation may be stored in memory 217 for later extraction or further analysis. Also, in one embodiment, real time or near real time communications may be provided to communicate the stimulation result or the stimulation log to an external unit 270.

Figure 7:
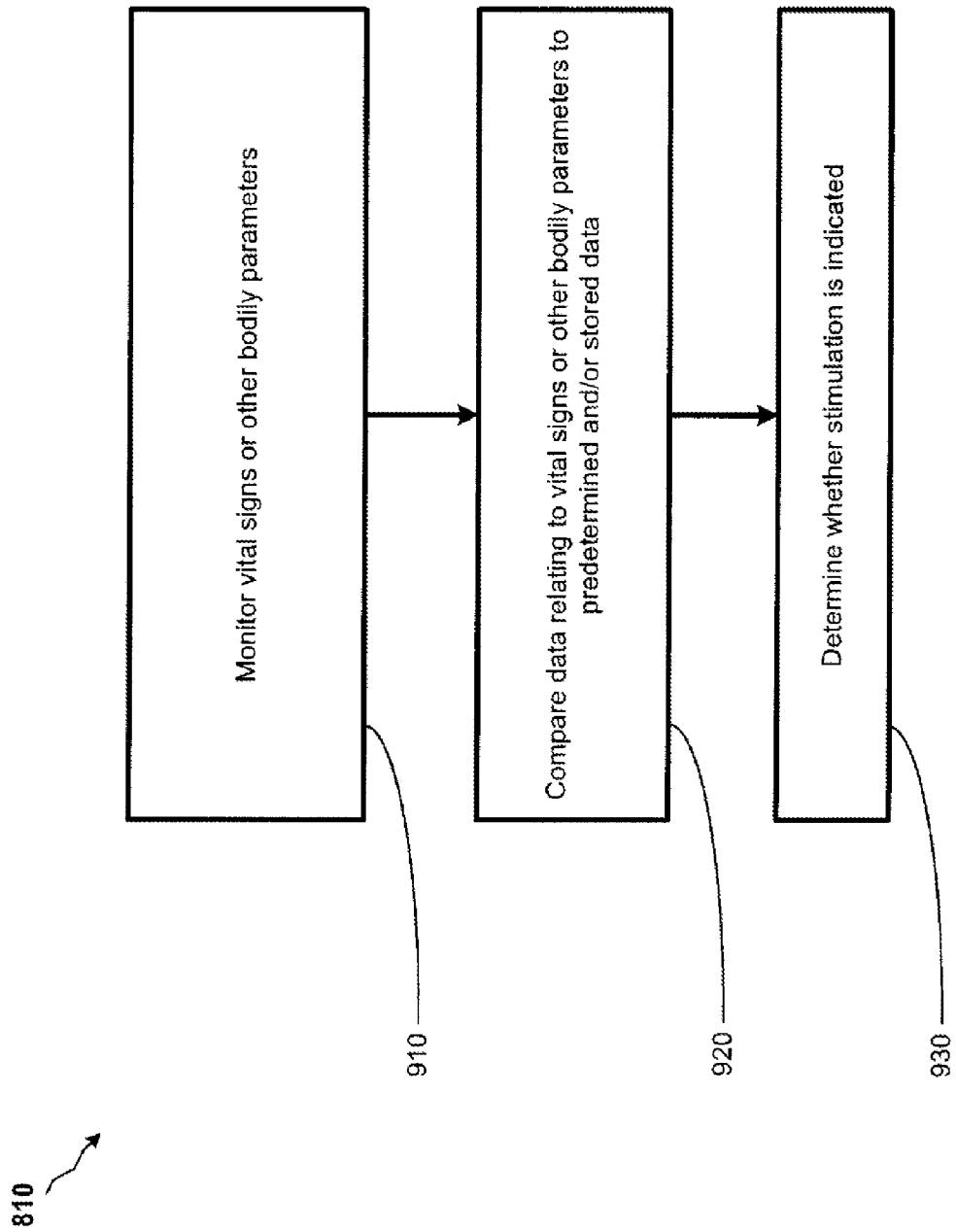
FIG. 7 depicts a more detailed flowchart depiction of the step of performing a detection process of FIG. 6, in accordance with an illustrative embodiment of the present invention.

Turning now to FIG. 7, a more detailed block diagram depiction of the step of performing the detection process of block 810 in FIG. 6, is illustrated. The system 100 may monitor one or more vital signs or other bodily parameters of the patient (block 910). This detection may be made by sensors residing inside the human body, which may be operatively coupled to the IMD 100. In another embodiment, these factors may be performed by external means and may be provided to the IMD 100 by an external device via the communication unit 260. In one embodiment, the sensors include a strain gauge that may be used to determine inspiration by identifying chest expansion. By detecting the onset of chest expansion, the strain gauge may detect the onset of inspiration. The strain gauge may also detect expiration by identifying when the chest is contracting.

Upon acquisition of various signals, a comparison may be performed comparing the data relating to the signals to predetermined, stored data (block 920). Based upon the comparison of the collected data with theoretical or stored thresholds, the IMD) 100 may determine whether an appropriate time to commence an on-time block has been reached (block 930). Based upon the determination described in FIG. 7, the IMD 100 may continue to determine whether further stimulation is indicated, as described in FIG. 6.

Additionally, external devices may perform such calculations and communicate the results or accompanying instructions to the IMD 100. The IMD 100 may also determine the specific location or branch of the nerve to stimulate. The IMD 100 may also indicate the type of stimulation to be delivered. For example, a microburst electrical signal alone or in combination with another type of treatment may be provided based upon the quantifiable parameter(s) that are detected. For example, a determination may be made that a microburst electrical signal by itself is to be delivered. Alternatively, based upon a particular type of medical condition, a determination may be made that a microburst electrical signal, in combination with a conventional therapeutic VNS signal, is desirable as a therapy for the patient.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method of treating congestive heart failure using an implantable medical device, the method comprising:
    applying a first electrical signal during a first stimulation period and applying a second electrical signal during a second stimulation period to a cranial nerve, wherein:
    the first electrical signal comprises:
        a pulse frequency;
        a first pulse width; and
        a first pulse amplitude; and
    the second electrical signal comprises:
        a plurality of microbursts applied at a microburst frequency, wherein at least one microburst comprises a plurality of microburst pulses applied during a first microburst duration, wherein each microburst pulse comprises:
            a second pulse width;
            a pulse shape; and
            a second pulse amplitude;
    wherein the first pulse width is different than the second pulse width and the first pulse amplitude is different than the second pulse amplitude and wherein a microburst has a microburst characteristic where the microburst characteristic includes at least one of: a number of electrical pulses being between 2 to 25 and a microburst duration of 10 milliseconds to 1 second.

2. The method of claim 1, wherein the first stimulation period and the second stimulation period are each a period of time.

3. The method of claim 1, wherein the first stimulation period comprises a predetermined number of pulses.

4. The method of claim 1, wherein the second stimulation period comprises a predetermined number of microbursts.

5. The method of claim 1, wherein the first stimulation period and the second stimulation period overlap.

6. The method of claim 1, wherein at least one of the first stimulation period and the second stimulation period is triggered based on a triggering event.

7. The method of claim 1, wherein each microburst comprises between 2 and 15 microburst pulses and the first microburst duration is from 10 milliseconds to 80 milliseconds.

8. The method of claim 1, wherein the cranial nerve is selected from:
    a vagus nerve;
    a trigeminal nerve; and
    a glossopharyngeal nerve.

9. An implantable medical device for treating congestive heart failure, the comprising:
    a controller, wherein the controller comprises a processor and a memory;
    a power supply; and
    a stimulation unit, wherein the stimulation unit being configured to apply a first electrical signal during a first stimulation period and a second electrical signal during a second stimulation period to a cranial nerve, wherein:
    the first electrical signal comprises:
        a first pulse frequency;
        a first pulse width;
        a first pulse shape; and
        a first pulse amplitude; and
    the second electrical signal comprises:
        a plurality of microbursts applied at a first microburst frequency, wherein at least one microburst comprises a plurality of microburst pulses applied during a first microburst duration, wherein each microburst pulse comprises:
            a second pulse width;
            a second pulse shape; and
            a second pulse amplitude;
        wherein the first pulse frequency is different than the first microburst frequency;
        wherein the first pulse width is different than the second pulse width;
        wherein the first pulse shape is different than the second pulse shape; and
        wherein the first pulse amplitude is different than the second pulse amplitude; and
    wherein a microburst has a microburst characteristic where the microburst characteristic includes at least one of: a number of electrical pulses being between 2 to 25 and a microburst duration of 10 milliseconds to 1 second.

10. The implantable medical device of claim 9, wherein the first stimulation period and the second stimulation period are each a period of time.

11. The implantable medical device of claim 9, wherein the first stimulation period comprises a predetermined number of pulses.

12. The implantable medical device of claim 9, wherein the second stimulation period comprises a predetermined number of microbursts.

13. The implantable medical device of claim 9, wherein the first stimulation period and the second stimulation period overlap.

14. The implantable medical device of claim 9, further comprising a detection unit, wherein at least one of the first stimulation period and the second stimulation period is triggered based on the detection unit detecting a triggering event.

15. The implantable medical device of claim 9, wherein each microburst comprises between 2 and 15 microburst pulses and the first microburst duration is from 10 milliseconds to 80 milliseconds.

16. The implantable medical device of claim 9, wherein the cranial nerve is selected from:
   a vagus nerve;
   a trigeminal nerve; and
   a glossopharyngeal nerve.

* * * * *